US008841602B2

(12) United States Patent
Schulte et al.

(10) Patent No.: US 8,841,602 B2
(45) Date of Patent: Sep. 23, 2014

(54) SYSTEMS, DEVICES AND METHODS RELATED TO CALIBRATION OF A PROTON COMPUTED TOMOGRAPHY SCANNER

(75) Inventors: Reinhard W. Schulte, Grand Terrace, CA (US); R. Ford Hurley, Loma Linda, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 95 days.

(21) Appl. No.: 13/413,499

(22) Filed: Mar. 6, 2012

(65) Prior Publication Data

US 2012/0273665 A1 Nov. 1, 2012

Related U.S. Application Data

(60) Provisional application No. 61/450,047, filed on Mar. 7, 2011.

(51) Int. Cl.
| | | |
|---|---|---|
| *G01D 18/00* | (2006.01) | |
| *G01N 23/04* | (2006.01) | |
| *A61B 6/00* | (2006.01) | |
| *A61B 6/03* | (2006.01) | |

(52) U.S. Cl.
CPC ............. *G01N 23/04* (2013.01); *A61B 6/032* (2013.01); *A61B 6/583* (2013.01)
USPC ...................................................... 250/252.1

(58) Field of Classification Search
USPC ...................................................... 250/252.1
See application file for complete search history.

(56) References Cited

U.S. PATENT DOCUMENTS

| 2,629,831 A | 2/1953 | Atchley, Jr. |
| 3,604,931 A | 9/1971 | Kastner et al. |
| 3,621,240 A | 11/1971 | Cohen et al. |

(Continued)

FOREIGN PATENT DOCUMENTS

| JP | 03094736 A | 4/1991 |
| WO | WO 87/00682 | 1/1987 |

(Continued)

OTHER PUBLICATIONS

Author: Scott Penfold, Title: Image reconstruction and Monte Carlo simulations in the development of proton computed tomography for applications in proton radiation therapy, Date: Dec. 17, 2010, Publisheer: University of Wollongong Thesis Collections.*

(Continued)

*Primary Examiner* — David Porta
*Assistant Examiner* — Taeho Jo
(74) *Attorney, Agent, or Firm* — Knobbe, Martens, Olson & Bear LLP

(57) ABSTRACT

Disclosed are systems, devices and methodologies related to calibration of an ion based imaging apparatus such as a proton computed tomography scanner. In some implementations, energy degrader plates having known water-equivalent thickness (WET) values can be introduced to an ion beam to introduce different energy degradation settings. Energy detector responses to individual ions subject to such energy degradation settings can be obtained. Such responses can be normalized and correlated to water-equivalent path lengths (WEPL) of the ions based on the known WET values. Such calibration utilizing degrader plates can be performed relatively quickly and can yield accurate WEPL values that facilitate estimation of, for example, a CT image based on relative stopping power of an object.

30 Claims, 14 Drawing Sheets

(56) References Cited

U.S. PATENT DOCUMENTS

| | | | |
|---|---|---|---|
| 3,901,588 A | 8/1975 | Longhenry | |
| 3,942,012 A | 3/1976 | Boux | |
| 3,955,089 A | 5/1976 | McIntyre et al. | |
| 3,975,640 A | 8/1976 | Boux et al. | |
| 3,986,026 A | 10/1976 | Martin | |
| 4,020,356 A | 4/1977 | Brahme | |
| 4,069,457 A | 1/1978 | Martin et al. | |
| 4,070,611 A | 1/1978 | Ernst | |
| 4,095,114 A | 6/1978 | Taumann | |
| 4,118,631 A | 10/1978 | Froggatt | |
| 4,190,772 A | 2/1980 | Dinwiddie et al. | |
| 4,206,355 A | 6/1980 | Boux | |
| 4,287,425 A | 9/1981 | Elliot, Jr. | |
| 4,602,622 A | 7/1986 | Bar et al. | |
| 5,115,391 A | 5/1992 | Puthenpura et al. | |
| 5,402,463 A | 3/1995 | Umetani et al. | |
| 5,446,548 A | 8/1995 | Gerig et al. | |
| 5,511,549 A | 4/1996 | Legg et al. | |
| 5,538,494 A | 7/1996 | Matsuda | |
| 5,553,112 A | 9/1996 | Hardy et al. | |
| 5,585,642 A | 12/1996 | Britton et al. | |
| 5,596,199 A | 1/1997 | McNulty et al. | |
| 5,596,619 A | 1/1997 | Carol | |
| 5,602,892 A | 2/1997 | Llacer | |
| 5,612,783 A | 3/1997 | Hirsh | |
| 5,622,170 A | 4/1997 | Schulz | |
| 5,777,325 A | 7/1998 | Weinberger et al. | |
| 5,825,845 A | 10/1998 | Blair et al. | |
| 5,851,182 A | 12/1998 | Sahadevan | |
| 5,963,658 A | 10/1999 | Klibanov et al. | |
| 5,981,946 A | 11/1999 | Mason | |
| 6,052,435 A | 4/2000 | Hernandez-Guerra et al. | |
| 6,104,779 A | 8/2000 | Shepherd et al. | |
| 6,148,272 A | 11/2000 | Bergstrom et al. | |
| 6,178,389 B1 | 1/2001 | Sola et al. | |
| 6,195,409 B1 | 2/2001 | Chang et al. | |
| 6,316,776 B1 | 11/2001 | Hiramoto et al. | |
| 6,345,114 B1 | 2/2002 | Mackie et al. | |
| 6,385,286 B1 | 5/2002 | Fitchard et al. | |
| 6,466,813 B1 | 10/2002 | Shukla et al. | |
| 6,473,490 B1 | 10/2002 | Siochi | |
| 6,694,057 B1 | 2/2004 | Miller et al. | |
| 6,754,299 B2 | 6/2004 | Patch | |
| 6,757,355 B1 | 6/2004 | Siochi | |
| 6,787,771 B2 | 9/2004 | Bashkirov et al. | |
| 6,799,068 B1 | 9/2004 | Hartmann et al. | |
| 6,804,548 B2 | 10/2004 | Takahashi et al. | |
| 7,081,619 B2 | 7/2006 | Bashkirov et al. | |
| 7,142,634 B2 | 11/2006 | Engler et al. | |
| 7,247,869 B2 | 7/2007 | Tadokoro et al. | |
| 7,268,358 B2 | 9/2007 | Ma et al. | |
| 7,398,309 B2 | 7/2008 | Baumann et al. | |
| 7,629,598 B2 | 12/2009 | Harada | |
| 7,801,270 B2 | 9/2010 | Nord et al. | |
| 7,820,989 B2 | 10/2010 | Sommer | |
| 8,045,679 B2 | 10/2011 | Balakin | |
| 8,080,801 B2 | 12/2011 | Safai | |
| 8,109,865 B2 | 2/2012 | Jackson | |
| 8,129,699 B2 | 3/2012 | Balakin | |
| 8,264,174 B2 | 9/2012 | Liu et al. | |
| 8,426,824 B2 * | 4/2013 | Jongen et al. | 250/370.01 |
| 2001/0016029 A1 | 8/2001 | Tumer | |
| 2002/0077545 A1 | 6/2002 | Takahashi et al. | |
| 2003/0007601 A1 | 1/2003 | Jaffray et al. | |
| 2003/0095625 A1 | 5/2003 | Steinberg | |
| 2003/0155530 A1 | 8/2003 | Adnani et al. | |
| 2004/0042583 A1 | 3/2004 | Wackerle et al. | |
| 2004/0158145 A1 | 8/2004 | Ghelmansarai et al. | |
| 2006/0104410 A1 | 5/2006 | Sauer et al. | |
| 2006/0166353 A1 | 7/2006 | Alfano et al. | |
| 2007/0031337 A1 | 2/2007 | Schulte | |
| 2007/0122020 A1 | 5/2007 | Claus et al. | |
| 2008/0031414 A1 | 2/2008 | Coppens | |
| 2008/0071131 A1 | 3/2008 | Rietzel | |
| 2008/0083871 A1 * | 4/2008 | Cravens et al. | 250/252.1 |
| 2008/0228418 A1 | 9/2008 | Green | |
| 2009/0168960 A1 | 7/2009 | Jongen et al. | |
| 2009/0196393 A1 | 8/2009 | Wang et al. | |
| 2009/0274269 A1 | 11/2009 | Foland et al. | |
| 2010/0032564 A1 | 2/2010 | Morris et al. | |
| 2010/0301235 A1 | 12/2010 | Bert et al. | |
| 2011/0006224 A1 | 1/2011 | Maltz et al. | |
| 2011/0220794 A1 | 9/2011 | Censor et al. | |
| 2011/0309255 A1 | 12/2011 | Bert et al. | |
| 2012/0056109 A1 | 3/2012 | Lomax | |
| 2012/0104270 A1 * | 5/2012 | Marchand et al. | 250/389 |
| 2012/0136194 A1 | 5/2012 | Zhang et al. | |
| 2012/0165651 A1 | 6/2012 | Inaniwa et al. | |
| 2012/0205557 A1 | 8/2012 | Rinecker | |
| 2012/0224667 A1 | 9/2012 | Cheng et al. | |
| 2013/0015352 A1 | 1/2013 | Karonis | |

FOREIGN PATENT DOCUMENTS

| | | |
|---|---|---|
| WO | WO 98/18523 | 5/1998 |
| WO | WO 03/020196 | 3/2003 |
| WO | WO 2007/095312 | 8/2007 |
| WO | WO 2008/067842 | 6/2008 |
| WO | WO 2008/140560 | 11/2008 |
| WO | WO 2009/135202 | 11/2009 |
| WO | WO 2010/011676 | 1/2010 |
| WO | WO 2010/149740 | 12/2010 |
| WO | WO 2011/100628 | 8/2011 |
| WO | WO 2011/154853 | 12/2011 |
| WO | WO 2011/162851 | 12/2011 |
| WO | WO 2012/024448 | 2/2012 |

OTHER PUBLICATIONS

Archambeau et al., "Conceptual Design of a Proton Therapy Synchrotron for Loma Linda University Medical Center," Fermi National Accelerator Laboratory, Jun. 1986, in 106 pages.

Archambeau et al., "Design of a Proton Therapy Synchrotron," Fermi National Accelerator Laboratory, Jun. 1986, pp. LL467-LL574 in 54 pages.

Censor, et al., "On Diagonally-Relaxed Orthogonal Projection Methods," SIAM Journal on Scientific Computing, vol. 30, pp. 473-504, (2008).

Cole et al., "Proceedings of a Medical Workshop on Accelerators for Charged-Particle Beam Therapy" by Fermilab, Jan. 24-25, 1985, LL33170-LL33313 in 144 pages.

Krause et al., "Adaption of a Synchrotron Control System for Heavy Ion Tumor Therapy", Proceedings of the 1995 International Conference on Accelerator and Large Experimental Physics Control Systems (ICALEPCS 1995), 1995, Chicago, Illinois, in 6 pages.

PCT/US2012/27911 International Search Report and Written opinion dated Nov. 28, 2012 in 14 pages.

S. Penfold, *Image Reconstruction and Monte Carlo Simulations in the Development of Proton Computed Tomography for Applications in Proton Radiation Therapy*, Doctor of Philosophy thesis, Centre for Medical Radiation Physics, University of Wollongong, 2010. Retrieved from the Internet http://ro.uow.edu.au/theses/3305; in 202 pages.

"Product Overview" by BrainLAB Radiotherapy Solutions, 2004, BrainLAB AG, in 6 pages.

"Proton Therapy Facility: Engineering Design Report," by Fermi National Accelerator Laboratory, Feb. 1987, LL45441-LL45570, in 130 pages.

Sadrozinski et al., Issues in Proton Computed Tomography, Nuclear Instruments and Methods in Physics Research A 511, Jun. 2003, pp. 275-281, in 7 pages.

Schulte et al., "Conceptual Design of a Proton Computed Tomography System for Applications in Proton Radiation Therapy," IEEE Transactions on Nuclear Science, Jun. 2004, pp. 866-872, vol. 51(3), in 7 pages.

Schulte et al., Nanoparticle-Enhanced Proton Computed Tomography: A Monte Carlo Simulation Study, Biomedical Imaging: Nano to Macro, 2004, IEEE International Symposium, Apr. 15-18, 2004, pp. 1354-1356 in 3 pages.

\* cited by examiner

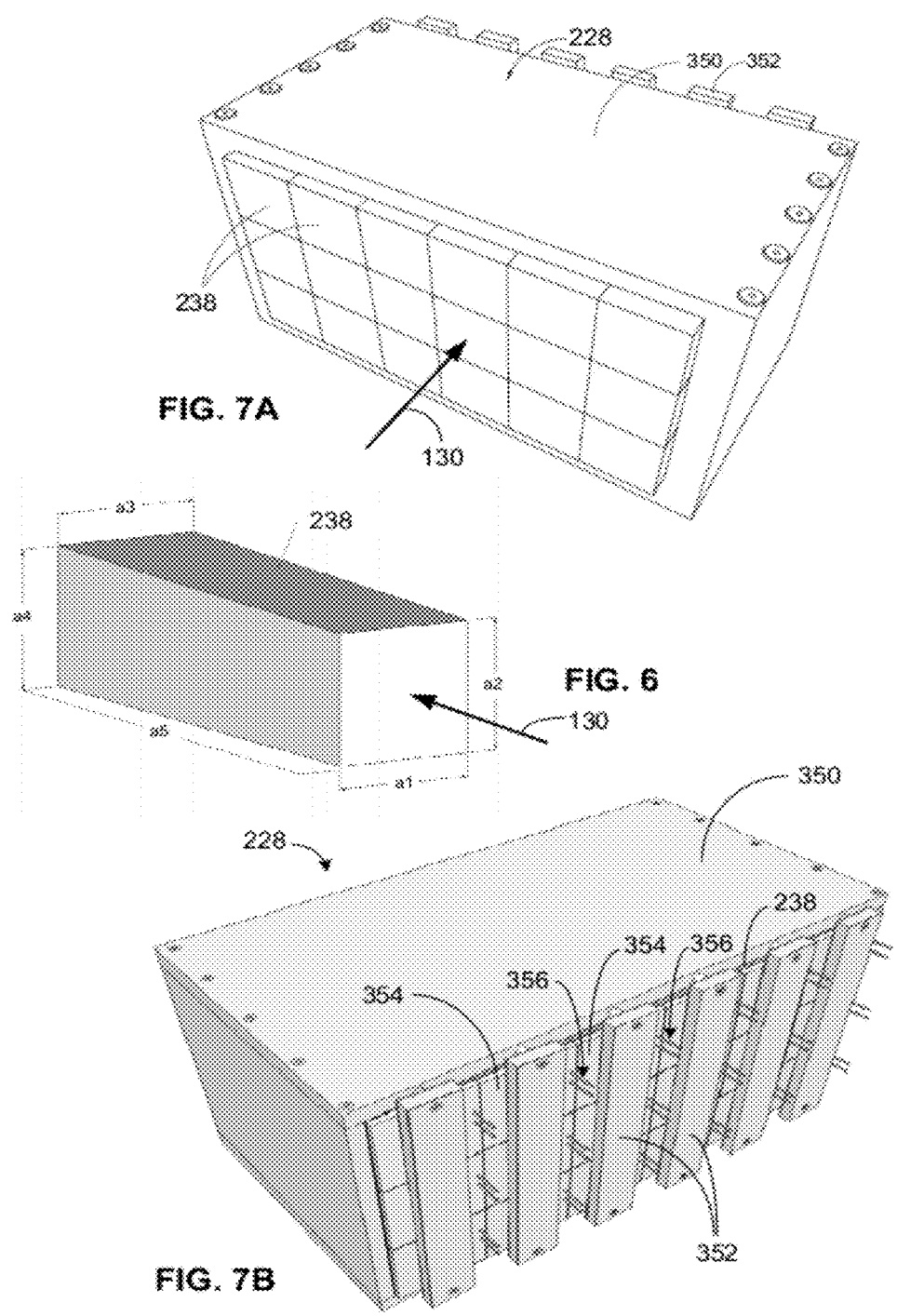

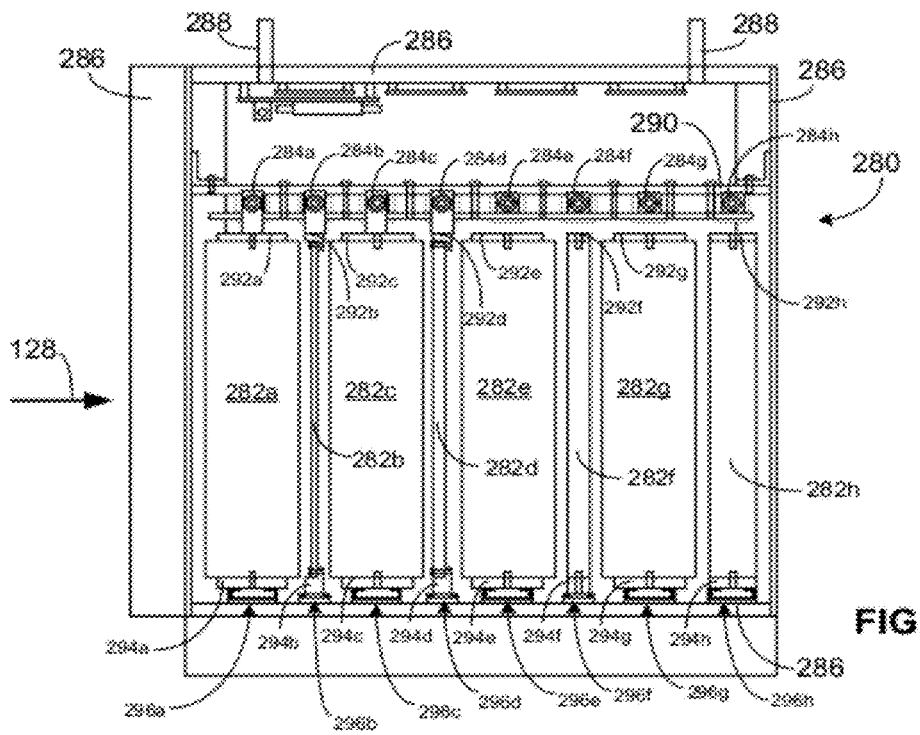
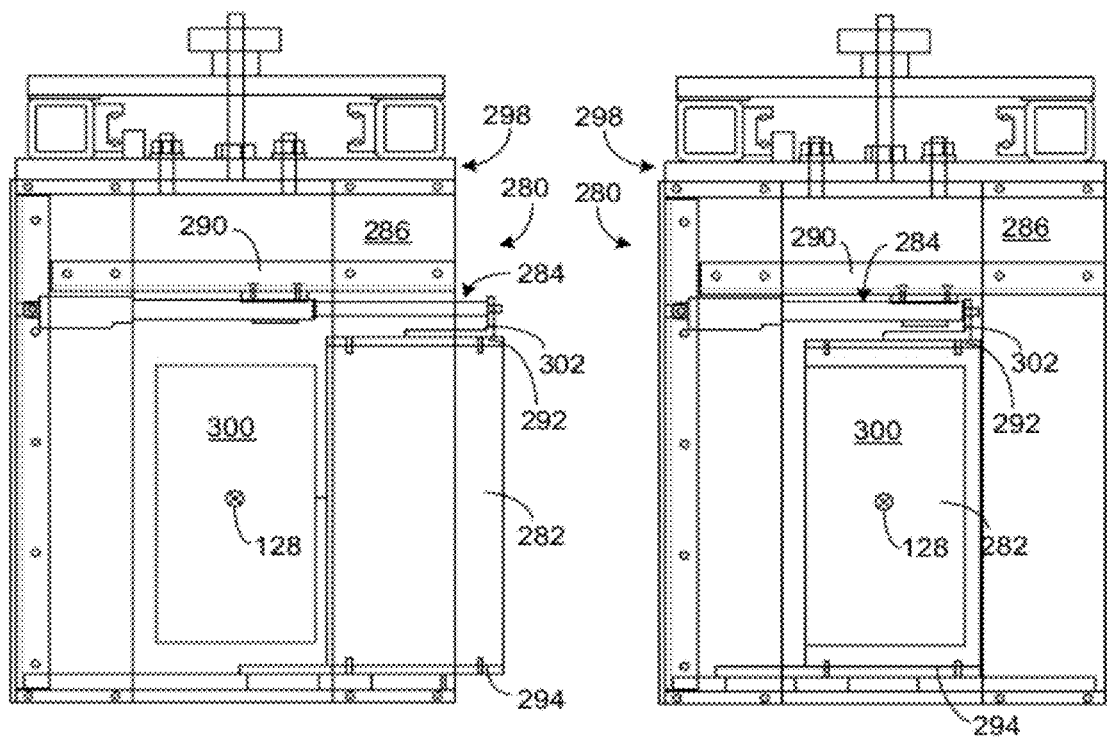
FIG. 10A
FIG. 10B
FIG. 10C

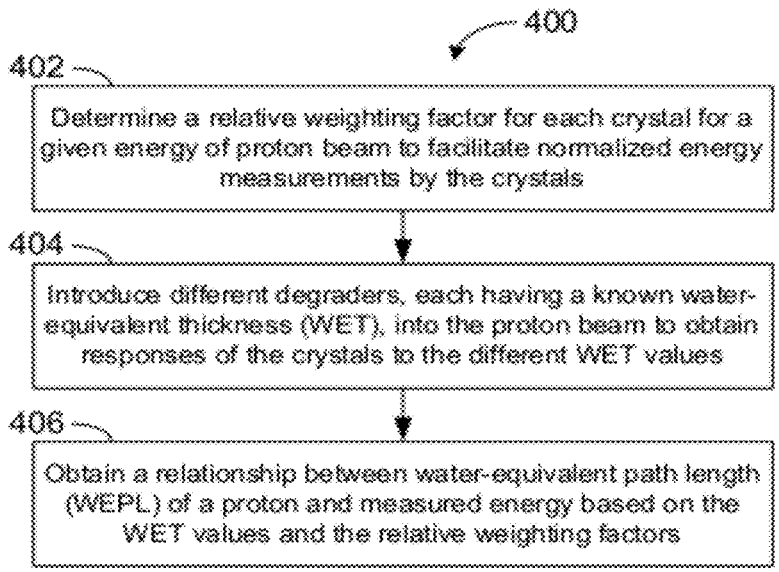
FIG. 13
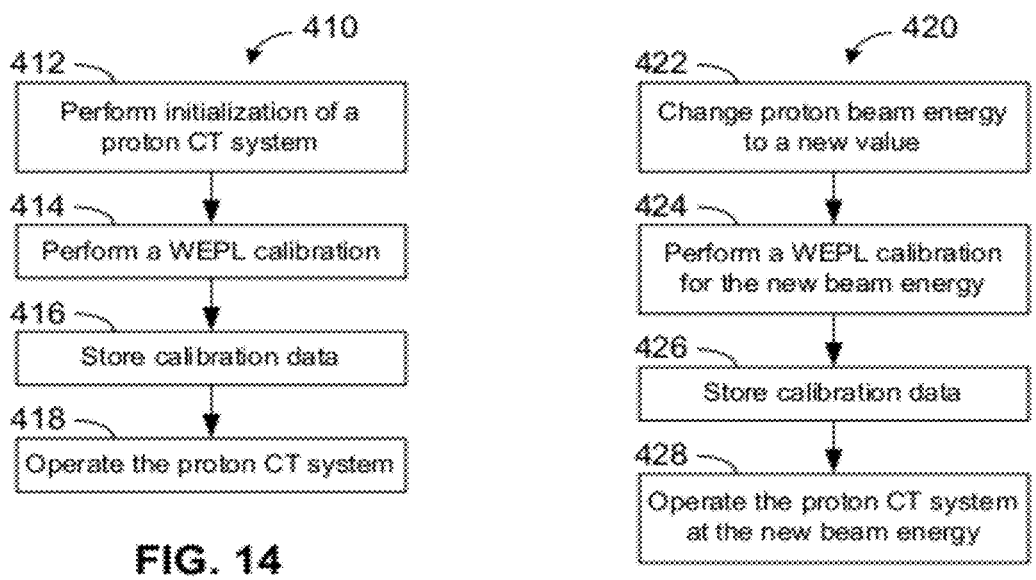
FIG. 14
FIG. 15

US 8,841,602 B2

SYSTEMS, DEVICES AND METHODS RELATED TO CALIBRATION OF A PROTON COMPUTED TOMOGRAPHY SCANNER

PRIORITY CLAIM

This application claims the benefit of priority of U.S. Provisional Patent Application No. 61/450,047, entitled "SYSTEMS AND METHODS FOR CALIBRATING A PROTON COMPUTED TOMOGRAPHY SCANNER," filed Mar. 7, 2011, which is hereby incorporated herein by reference in its entirety to be considered part of this specification.

STATEMENT REGARDING FEDERALLY SPONSORED R&D

This invention was funded, in part, by government support under NIH Grant No. 1R01EB013118-01 and DOD Contract No. W81XWH0-08-1-0205. The government has certain rights in the invention.

BACKGROUND

1. Field

The present disclosure generally relates to the field of medical imaging, and more particularly, to systems, devices and methodologies related to calibration of a proton computed tomography scanner.

2. Description of the Related Art

Energetic ions such as protons can be used to form images of an object such as a portion of a patient. Such ion-based imaging can include, for example, computed tomography (CT).

CT images generated by use of protons can be based on a distribution of relative stopping power (RSP) associated with the object. An accurate measurement of energy loss of protons resulting from passage through the object can yield an improved reconstruction of the RSP distribution of the object.

SUMMARY

In some implementations, the present disclosure relates to a method for calibrating a proton computed tomography scanner. The method includes performing, for each of a plurality of energy degradation settings: introducing one or more degrader plates into a beam of protons having energy E, the one or more degrader plates in combination having a known water-equivalent thickness (WET) value; and obtaining signals from an energy detector for each of a plurality of selected protons that have passed through the one or more degrader plates and captured by the energy detector. The method further includes calculating a weighted response of the energy detector based on at least some of the signals and one or more weighting factors associated with the energy detector. The method further includes generating a relationship between the weighted response and water-equivalent path length (WEPL) based on the known WET values associated with the plurality of energy degradation settings.

In some implementations, the method can further include storing information representative of the relationship in a non-transitory computer-readable medium. In some implementations, introducing the one or more degrader plates can include positioning one or more substantially parallel polystyrene plates into the beam of protons such that the plates are approximately perpendicular to a longitudinal axis of the beam of protons. The WET values associated with the plurality of degradation settings can be in a range between zero and an upper limit that yields a weighted response about 10% of a maximum weighted response obtained without any degrader plate.

In some implementations, the energy detector can include a segmented calorimeter having a plurality of crystals such that the calorimeter includes a plurality of channels corresponding to the plurality of crystals. In some embodiments, each of the crystals can include a cesium iodide (CsI) crystal. The plurality of selected protons can include protons that pass a proton event cut and having calculated most likely path lengths within Y% of a path length corresponding to the known WET value. The value of Y can be, for example, approximately 0.5. The proton event cut can include one or more of excluding events where the proton was scattered out of the scanner, where proton tracking information is ambiguous, and where the proton did not pass through all tracking planes of the scanner.

In some implementations, the beam of protons can include a cone beam dimensioned to allow hits of the selected protons at each of the crystals of the segmented calorimeter. In some implementations, the one or more weighting factors can include a weighting factor $w_i$ for the i-th channel of the calorimeter. The i-th weighting factor $w_i$ can be represented as, for example, $w_i = (\text{scale factor})/\langle r \rangle_i$, where the scale factor is selected to provide a desired scale of values for the weighted response of the energy detector, and $\langle r \rangle_i$ represents an average signal of the i-th channel when the crystals are subjected to selected undegraded protons. The selected undegraded protons can include protons that do not pass through any degrader and enter at center portions of and at directions generally parallel to their respective crystals. The scale factor can be proportional to the beam energy E. The scale factor can be selected to be $C*E$, where C is a constant selected so that a mean weighted sum of all of the channels yields a desired value.

In some implementations, the weighted response of the energy detector can include a weighted sum of signals from selected channels. Each of the signals can have a value higher than $3\sigma$ above a noise floor value. The selected channels can include a high value channel having the largest signal, and channels corresponding to crystals immediately surrounding the crystal of the high value channel.

In some implementations, the relationship between the weighted response and WEPL can include a fit based on data points corresponding to the plurality of energy degradation settings. The fit can include a fit of a second-degree polynomial.

In some implementations, the present disclosure relates to a proton computed tomography scanner that includes a tracker configured to facilitate tracking of individual protons of a beam before and after passage through a target region. The scanner further includes an energy detector configured to detect energy of the individual protons that have passed through the target region. The scanner further includes a calibration device configured to be positionable at or near the target region and allow introduction of a plurality of energy degradation settings for the beam or protons. The calibration device includes a plurality of degrader plates configured to allow introduction one or more of the degrader plates into the beam, with the one or more degrader plates in combination having a known water-equivalent thickness (WET) value. The scanner further includes a data acquisition system configured to obtain signals from the energy detector for each of a plurality of selected protons that have passed through the one or more degrader plates and captured by the energy detector. The scanner further includes a processor configured to: calculate a weighted response of the energy detector based on at least some of the signals and one or more weighting factors associated with the energy detector; and generate a relationship between the weighted response and water-equivalent path length (WEPL) based on the known WET values associated with the plurality of energy degradation settings.

In some embodiments, the energy detector can include a segmented calorimeter having a plurality of crystals such that the calorimeter includes a plurality of channels corresponding to the plurality of crystals. In some embodiments, each of the crystals can include a cesium iodide (CsI) crystal.

In some embodiments, the tracker can include a front tracker having a plurality of detections planes of silicon strips, and a rear tracker having a plurality of detection planes of silicon strips. In some embodiments, the calibration device can include an actuator mechanically coupled to each of the plurality of degrader plates so as to allow remote controlling of the introduction of the one or more of the degrader plates into the beam. In some embodiments, each the plurality of degrader plates can be a polystyrene plate.

In some implementations, the present disclosure relates to a calibration device for an ion based imaging system. The calibration device includes a frame configured to allow the calibration device to be positioned at a target region of the imaging system and allow a beam of ions pass through the target region. The calibration device further includes a plurality of degrader plates configured to be movable into and out of the beam of ions, with each degrader plate having a known water-equivalent thickness (WET) value such that combinations of the degrader plates allow introduction of a plurality of energy degradation settings for the beam of ions and estimation of a relationship between response associated with measurement of residual energy of individual ions and water-equivalent path length (WEPL).

In some embodiments, the calibration device can further include a plurality of actuators mechanically coupled to the plurality of degrader plates so as to allow remote controlling of the introduction of the energy degradation settings. In some implementations, the ions can include protons. In some implementations, the imaging system can include a computed tomography imaging system.

For purposes of summarizing the disclosure, certain aspects, advantages and novel features of the inventions have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

FIG. 6 shows an example configuration of a calorimeter crystal for measuring energy of protons that have passed through an object.

FIG. 7A shows a front perspective view of an example energy detector having a plurality of crystals of FIG. 6.

FIG. 7B shows a rear perspective view of the energy detector of FIG. 7A.

FIGS. 10A-10C show additional details of the calibration system of FIG. 9.

FIG. 13 shows a process that can be implemented to obtain a calibration relationship between water-equivalent path length (WEPL) and response of the energy detector.

FIG. 14 shows that in some implementations, the calibration process of FIG. 13 can be performed as part of an initialization of a pCT system.

FIG. 15 shows that in some implementations, the calibration process of FIG. 13 can be performed when the beam energy of a pCT is changed.

DETAILED DESCRIPTION OF SOME EMBODIMENTS

Figure 1:
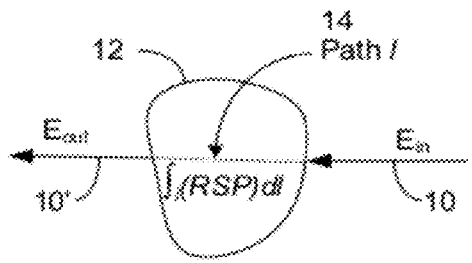
FIG. 1 schematically depicts an energetic ion such as a proton passing through an object and losing energy due to a distribution of relative stopping power (RSP) of the object.

The headings provided herein, if any, are for convenience only and do not necessarily affect the scope or meaning of the claimed invention.

Provided herein are various examples of systems, devices and methodologies related to calibration of proton-based imaging apparatus such as a proton computed tomography (pCT) scanner. Although described in the context of such a pCT scanner, it will be understood that one or more features described herein can also be utilized in other imaging apparatus such as a proton radiograph apparatus.

Also, various features and examples described herein are in the context of protons. It will be understood that one or more features described herein can also be implemented in systems that use other energetic ions, including but not limited to carbon ions.

Proton computed tomography (pCT) involves reconstruction of tomographic images with protons of sufficient energy to penetrate a patient. PCT can be more accurate than X-ray CT in providing relative stopping power (RSP) distributions in the patient without the need for converting Hounsfield units to RSP, and may, therefore, be used instead of X-ray CT for applications such as proton treatment planning.

In some implementations, pCT scanning and image reconstruction can be based on measurement of energy loss of protons resulting from passage of the protons through an object being scanned. Protons can also be used to perform proton radiography for 2D imaging based on protons traversing an object. Proton radiography can be utilized as, for example, a tool for quality assurance in X-ray-CT-planned proton treatment or to quantify proton range variations during respiration.

By measuring the energy loss or residual range of protons after they interacted with an object such as a portion of a patient, a water-equivalent path length (WEPL) distribution across the object can be inferred. Obtaining such a WEPL distribution typically involves conversion of a detector response to an integral of the object's RSP along the path/of the proton. Such a conversion can be based on a relationship $$L = \int_l \varrho \, dl \quad (1)$$

where L represents WEPL, and $\rho$ is defined as a ratio of the local stopping power of the material of the object, $S_m$, to the stopping power of water, $S_w$:

$$\varrho = \frac{S_m}{S_w}. \quad (2)$$

It is noted that, for proton energies in a range between about 30 MeV and 250 MeV, variation of RSP with proton energy is generally negligible. For example, for brain tissue (as defined by the International Commission on Radiological Protection (ICRP)) the difference of the RSP at 30 MeV and 200 MeV is only about 0.07%. For practical purposes, one can, therefore, consider $\rho$ as being generally independent of proton energy.

Assuming that the residual energy of protons (after passing through the object) is known, an estimate of the WEPL, L, can be obtained by numerically solving an integral of the reciprocal of the stopping power of protons in water $$L = \int_{E_{out}}^{E_{in}} \frac{1}{S(I_w, E)} \, dE, \quad (3)$$

where $E_{in}$ is the incoming energy of the proton and $E_{out}$ is the outgoing energy. $S(I_w, E)$ is the stopping power of water for protons of energy E and $I_w$ is the mean excitation energy of water. The stopping power in the energy range above 10 MeV can be described appropriately by the Bethe-Bloch equation.

The use of Equation 3 requires knowledge of the outgoing energy of protons after traversing the object. Described herein are examples of how a calorimeter (such as a thallium-doped cesium iodide (CsI(Tl)) crystal-based calorimeter) can be calibrated so as to allow accurate determination of the outgoing energy of proton. In some implementations, such calibration can be based on known degrader plates having known water-equivalent thickness (WET) values.

FIG. 1 depicts an object 12 being imaged. An input proton 10 having energy $E_{in}$ is shown to pass through the object 12 along a path l (14) and exit the object as an output proton 10' with energy $E_{out}$. As described above in reference to Equations 1-3, an integral of the object's RSP along the proton's path l (14) is proportional to the WEPL of the object 12. Such an integral can be evaluated between input and output energies ($E_{in}$ and $E_{out}$). The input energy $E_{in}$ is typically known, and the output energy $E_{out}$ is typically measured by signals generated a calorimeter in response to the output proton. Accordingly, an accurate calibration of the calorimeter's response signals can yield more accurate determination of the object's distribution of RSP.

Figure 2:
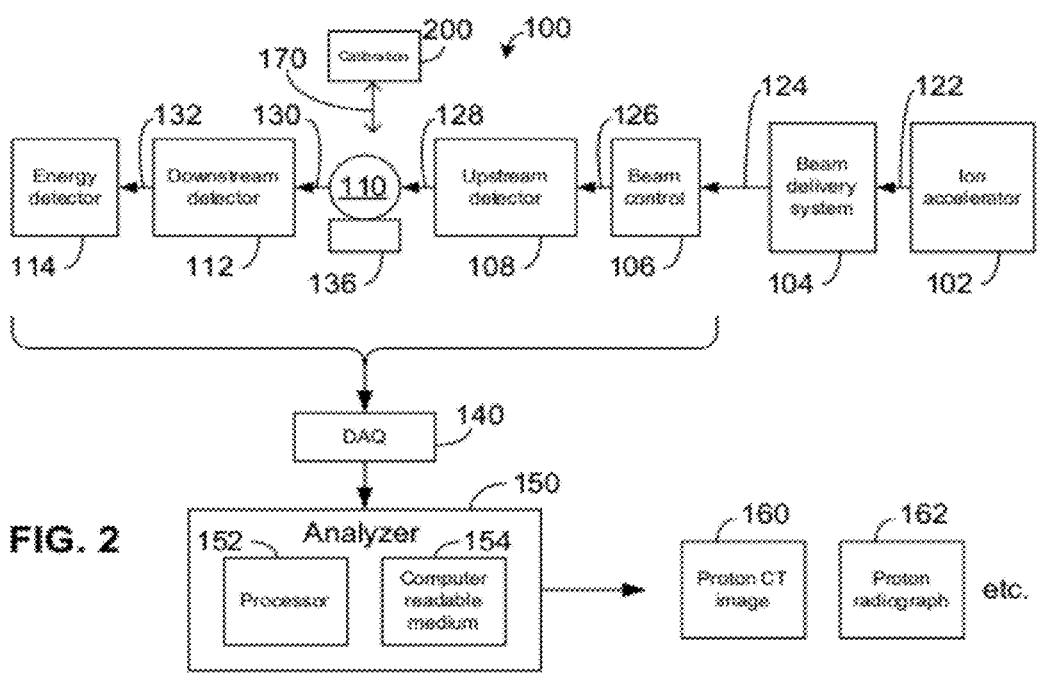
FIG. 2 shows an imaging system that can be configured to operate based on the stopping power principle of FIG. 1.

FIG. 2 shows an example system 100 configured to provide therapy and/or imaging functionality. The system 100 can include an ion accelerator 102 configured to generate an energetic beam 122 of ions. Such an accelerator can include a linear accelerator, a cyclic accelerator such as a cyclotron or a synchrotron, or any combination thereof. As described herein, the accelerator's output beam 122 can include a proton beam; however, other ion beams (such as carbon ion beam) can also be utilized.

The accelerator's output beam 122 can be delivered to a desired location by a beam delivery system 104. Such a delivery system can be configured in a number of known ways so as to yield a delivered beam 124. Such a beam can then be manipulated by a beam control component 106 to yield an input beam 126 for therapy and/or imaging purpose.

The input beam 126 is shown to be delivered to an object 110 being treated or imaged. In some implementations, the object 110 can be mounted and/or held by or on a mount 136. In the context of imaging applications, a beam 130 emerging from the object 110 is shown to be accepted by an energy detector 114 as beam 132.

Vectors associated with protons of the input beam 126 (before entering the object 110) and the emerging beam 130 can be characterized by an upstream detector 108 and a downstream detector 112, respectively. Examples of such detectors are described herein in greater detail.

Signals representative of energies and vectors of the input protons and emerging protons can be obtained from, for example, the upstream detector 108, the downstream detector 112 and the energy detector 114. Reading out and processing (e.g., analog-to-digital conversion) of such signals can be achieved by a data acquisition (DAQ) system 140. Data representative of such processed signals can then be analyzed by an analyzer 150 that includes, for example, a processor 152 and a computer readable medium (CRM) 154. The analyzer 150 can yield data representative of, for example, a pCT image 160, a proton radiograph, etc.

In some implementations, a processor as described herein can be configured to facilitate implementation of various processes described herein. For the purpose of description, embodiments of the present disclosure may also be described with reference to flowchart illustrations and/or block diagrams of methods, apparatus (systems) and computer program products. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the acts specified in the flowchart and/or block diagram block or blocks.

In some embodiments, these computer program instructions may also be stored in a computer-readable medium (e.g., 154 in FIG. 2) that can direct a computer or other programmable data processing apparatus to operate in a particular manner, such that the instructions stored in the computer-readable medium produce an article of manufacture including instruction means which implement the acts specified in the flowchart and/or block diagram block or blocks. The computer program instructions may also be loaded onto a computer or other programmable data processing apparatus to cause a series of operations to be performed on the computer or other programmable apparatus to produce a computer implemented process such that the instructions that execute on the computer or other programmable apparatus provide steps for implementing the acts specified in the flowchart and/or block diagram block or blocks.

As further shown in FIG. 2, a calibration component 200 can be configured to facilitate calibration of the system 100 in a manner as described herein. In some implementations, some or all portions of the calibration component 200 can be configured to be moved in and out (arrow 170) of the beam line. For such a configuration, some or all portions of the calibration component 200 can be positioned in the beam line at or near a location where the object 110 would be.

Figure 3:
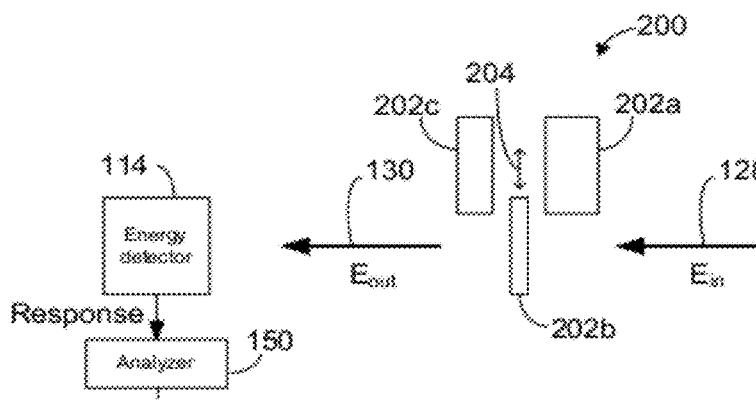
FIG. 3 shows a more detailed view of a calibration system that can be implemented in the imaging system of FIG. 2.

FIG. 3 schematically depicts an example configuration of the calibration component 200. One or more proton energy degraders 202 having a known effective thickness (such as a water-equivalent thickness (WET)) can be introduced into an input beam 128 of protons having energy $E_{in}$. In the example shown, a degrader 202b is shown to be introduced (arrow 204) into the beam 128, while degraders 202a and 202c remain out of the beam 128. Accordingly, the effective thickness for such a configuration can be represented by the thickness of the degrader 202b.

The input beam 128 that passes through the one or more degraders is shown to emerge as an emerging beam 130 of protons having energy $E_{out}$. Energy values of such protons can be measured by the energy detector 114, and the detector 114 can generate signals in response to the protons. Such response signals can be processed by the analyzer 150 so as to yield an equivalent path length (such as water-equivalent path length (WEPL)). Disclosed herein are various examples of how such the calibration component 200 and the energy detector 112 can be configured and operated so as to yield a WEPL relationship between the WEPL and the response of the energy detector 114.

Figure 4:
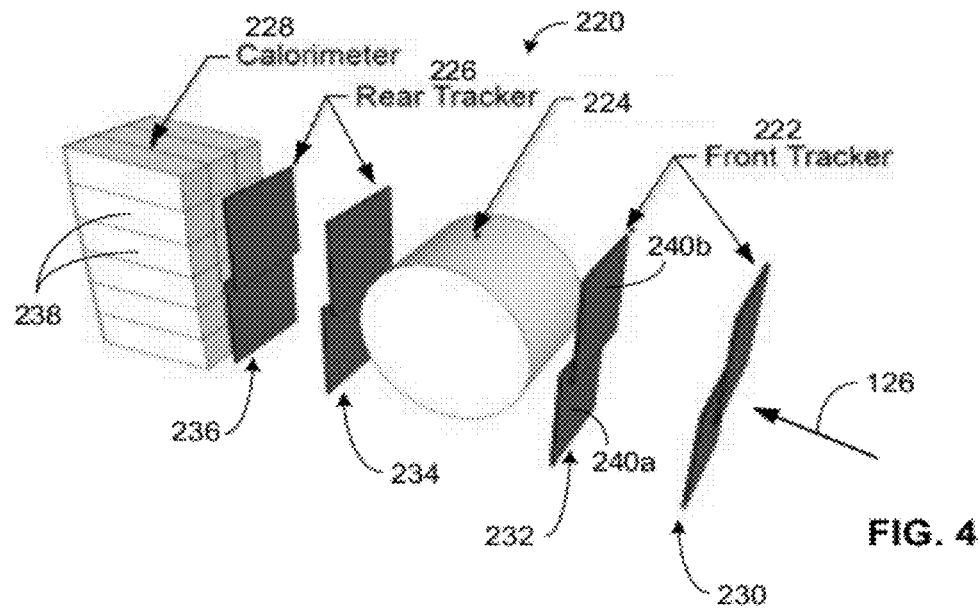
FIG. 4 shows an example proton computed tomography (pCT) scanner that can be an example of the imaging system of FIG. 1.

FIG. 4 shows an example of a pCT scanner 220 for which one or more calibration features as described herein can be implemented. The scanner 220 is shown to receive an input beam 126 of protons directed at an object 224 being imaged. Determination of vectors associated with the beam of protons before entry into the objet 224 can be facilitated by an upstream detector (also referred to as a front tracker herein) 222. Determination of vectors associated with the beam of protons emerging from the objet 224 can be facilitated by a downstream (also referred to as a rear tracker herein) 226. Energy values associated with the emerging protons can be measured by an energy detector (also referred to as a calorimeter herein) 228. The example calorimeter 228 is shown to include a plurality of modules 238 configured and arranged so as to provide segmentation functionality.

The front tracker 222 is shown to include first and second detector planes 230, 232. Each of the first and second detector planes 230, 232 is shown to include slight overlap of sensitive planes (e.g., 240a, 240b) so as to provide continuous sensitive areas without a gap. Each of the sensitive planes includes silicon strip detectors arranged as X- and Y-resolving planes, each with a sensitive area of approximately 8.95×17.4 cm$^2$ and a strip pitch of approximately 228 μm.

Similarly, the rear tracker 226 is shown to include first and second detector planes 234, 236. Each of the first and second detector planes 234, 236 is shown to include slight overlap of sensitive planes (e.g., 240a, 240b) so as to provide continuous sensitive areas without a gap. Each of the sensitive planes includes silicon strip detectors arranged as X- and Y-resolving planes, each with a sensitive area of approximately 8.95×17.4 cm$^2$ and a strip pitch of approximately 228 μm.

Accordingly, the front tracker 222 includes eight silicon strip detectors (four per each of the two detector planes 230, 232), and the rear tracker 226 includes eight silicon strip detectors (four per each of the two detector planes 234, 236). It will be understood that a number of other tracking detection devices and methodologies can also be utilized.

The example calorimeter 228 includes 18 thallium-doped cesium iodide (CsI(TI)) crystals 238 arranged to form a 3×6 rectangular matrix encompassing the sensitive area of the tracker 226. It will be understood that a number of other energy detection devices and methodologies can also be utilized.

Figure 5:
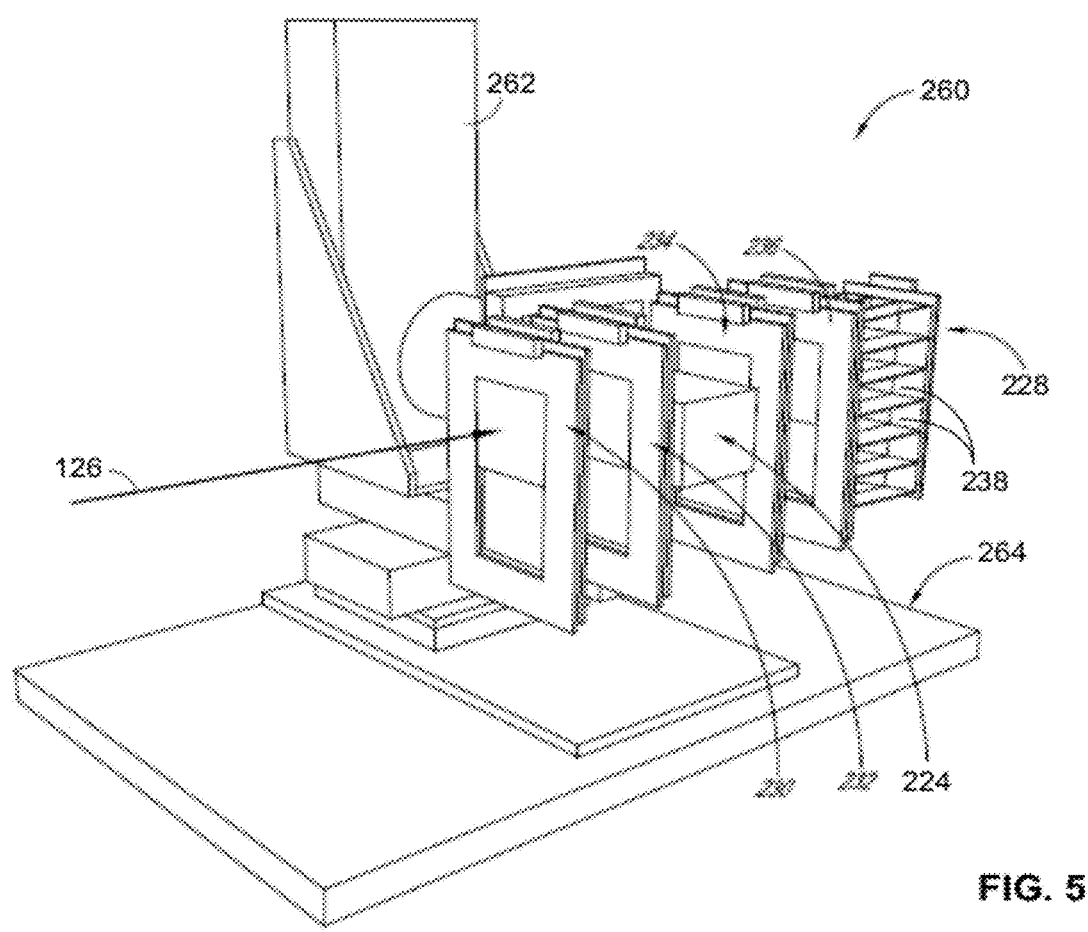
FIG. 5 shows an example of how the pCT scanner of FIG. 4 can be mounted relative to a beam of protons.

FIG. 5 shows an example configuration 260 where the pCT scanner 220 of FIG. 4 is mounted on a mounting structure 262 which is in turn mounted on a stable platform 264. The detector planes 230, 232, 234, 236, as well as the calorimeter 228 and its crystals 238 can be configured as described in reference to FIG. 4.

In the example shown in FIG. 5, the detector assembly that includes the front and rear trackers and the calorimeter can be mounted appropriately so as to be substantially fixed relative to the beam 126 when in operation. The object 224 being imaged can be mounted to the mounting structure 262 so as to allow rotation (e.g., about an axis perpendicular to the beam axis) to facilitate tomographic imaging. In some implementations, a tomographic imaging scanner having one or more features as described herein can be configured so that an object being scanned rotates relative to detectors, detectors rotate about an object being scanned, or any combination thereof.

FIGS. 6 and 7 show additional details of the example calorimeter 228. As described in reference to FIGS. 4 and 5, the example calorimeter 228 includes 18 thallium-doped cesium iodide (CsI(TI)) crystals 238 arranged to form a 3×6 rectangular matrix encompassing the sensitive area of the tracker 226. There are a number of reasons why a segmented calorimeter can be advantageous over a mono-crystal design. For example, with a segmented calorimeter in combination with the tracker it is possible to calibrate the response of individual crystals decreasing the effect of non-uniformity across the calorimeter. In another example, the cross section of individual crystals can be dimensioned to substantially match that of individual photodiodes that detect light generated in the crystals, thus generally improving light collection efficiency. In yet another example, segmenting the calorimeter can reduce the pile-up rate thus increasing the proton counting rate.

In the example calorimeter 228, each crystal 238 is approximately 12.5 cm long (dimension a5 in FIG. 6), which is generally sufficient to stop 200 MeV protons. Other dimensions of the example crystal 238 can have the following approximate values: a1=a2=34 mm, and a3=a4=36 mm. The slight wedge shape of the crystal 238 allows an assembly of crystals to generally point at an upstream target location, such as a center of the object, so that a proton entering each crystal (represented by arrow 130) can be generally parallel or nearly parallel to the crystal's longitudinal axis.

FIG. 7A shows a front perspective view of the calorimeter 228, and FIG. 7B shows a rear perspective view of the same. In some embodiments, the calorimeter 228 can include a housing 350 dimensioned to hold an array of stacked crystals 238. Because of the slight wedge shape of each crystal 238, an assembly of such crystals also yields a wedge shape where the rear lateral dimension is greater than the front lateral dimension. Accordingly, the housing having dimensions to accommodate such a wedge shape can retain the crystals 238 while providing an exposed front surface to receive protons (arrow 130).

As shown in FIG. 7B, the rear portion of the housing 350 is shown to include retaining plates 352 dimensioned to securely hold the rear portions of the crystals 238 and their corresponding photo-detectors (e.g., photodiodes) 354. The retaining plates 352 are also shown to allow providing of power and reading out of signals to and from the photodetectors 354 via connectors 356.

In the example calorimeter configuration of FIGS. 6 and 7, residual energy of protons stopping in the calorimeter is converted to light by scintillation. The light can be collected by the photodiodes 354 paired to their respective crystal 238 to generated analog signals. Such analog signals can be converted to digital values with one or more analog digital converters (ADC).

Signals and/or digital data from the calorimeter 228 and the tracker (222, 226) can be read out and/or further processed by a data acquisition (DAQ) system. For the example configurations described herein, an FPGA (field-programmable gate array) based DAQ system can process and record both the tracking and energy information at a rate up to approximately $10^5$ protons per second. With higher proton rates, the pile-up rate can increase, thereby reducing the overall acquisition rate of events having desired proton histories.

Data acquired in the foregoing manner can be analyzed to yield, for example, a CT image. Such an analysis can include tomographic reconstruction algorithms including but not limited to parallelizable algorithms configured for implementation on graphics processing units (GPUs). Such reconstruction algorithms can include, for example, algorithms that utilize energy loss measurements of individual protons and most likely path (MLP) techniques to yield tomographic reconstructions with sufficient spatial resolution, despite the effect of multiple Coulomb scattering. Such reconstructions can also include methodologies and techniques where a matrix representative of MLPs and object voxel index, along with a vector having WEPL of individual protons from the calorimeter response, are utilized so as to generate a solution representative of a distribution of RSP in the object being imaged. Such generation of a solution can include, for example, use of an algebraic reconstruction technique (ART) and superiorization methods. Additional details concerning some or all of the foregoing reconstruction features can be found in, for example, U.S. Patent Publication No. 2011-0220794, entitled "SYSTEMS AND METHODOLOGIES FOR PROTON COMPUTED TOMOGRAPHY," which is hereby incorporated herein by reference in its entirety.

Figure 8:
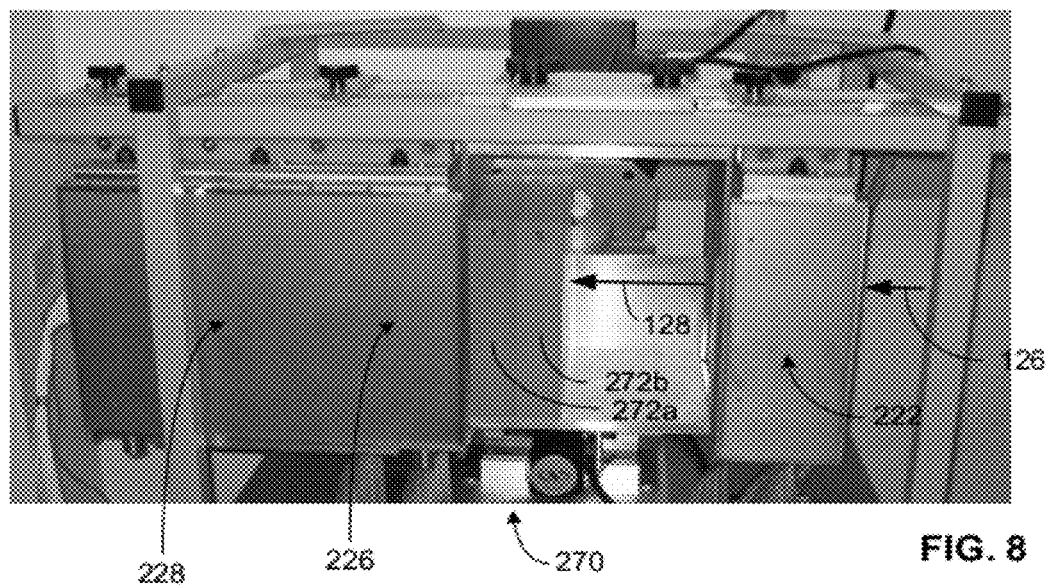
FIG. 8 shows the example pCT scanner of FIG. 4 with an example configuration of the calibration system of FIG. 3.
Figure 9:
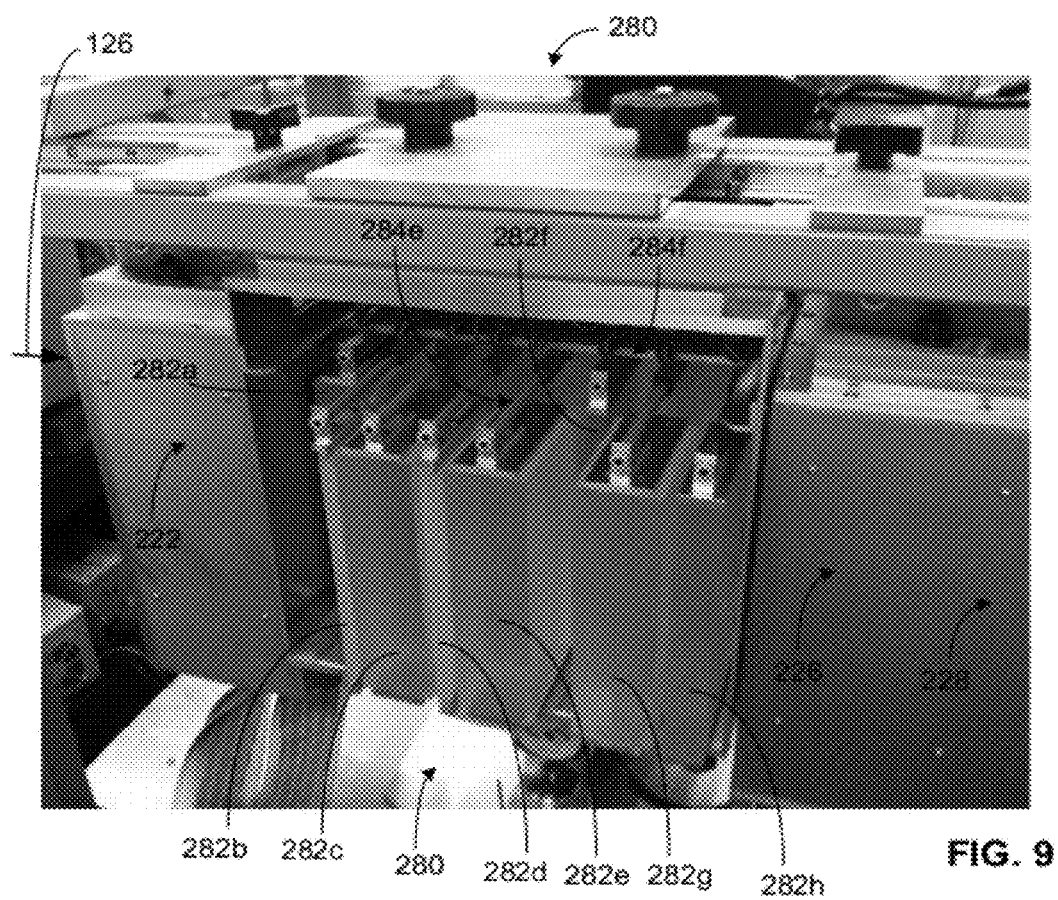
FIG. 9 shows the example pCT scanner of FIG. 4 with another example configuration of the calibration system of FIG. 3.

As described herein, obtaining accurate WEPL values from calorimeter responses is generally desirable. FIGS. 8 and 9 show examples of calibration components that can be utilized to facilitate obtaining of such accurate WEPL values. FIG. 8 shows an example configuration where degrader plates (e.g., 272a, 272b) can be positioned manually along a beam path. FIG. 9 shows an example configuration where degrader plates (e.g., 282a-h) can be positioned along a beam path in a selected manner by their respective actuators 284. Such a configuration can allow introduction of different degrader plates in the beam path from a remote location; and thus can be configured for automatic operation.

In both example configurations (270, 280), the assembly of degrader plates (272, 282) are positioned along a beam 128 of protons that have passed through the front tracker 222 (which receives a beam 126 of input protons). The beam of protons 128 is can pass through one or more degraders and pass through the rear tracker 226. Such protons can then be captured by the calorimeter 228 so as generate response signals representative of the protons' residual energy remaining after passage through the degrader plate(s).

FIGS. 10A-10C show different views of the example calibration device 280 described in reference to FIG. 9. FIG. 10A shows a side view of the calibration device 280 with the beam of protons 128 entering from the left as shown. FIG. 10B shows a longitudinal view along the direction of the beam 128 with an example degrader plate 282 out of the beam's path. FIG. 10C shows the same longitudinal view with the example degrader plate 282 in the beam's path.

In FIGS. 10A-10C, various thickness degrader plates 282a-282h are shown to be mounted to their respective actuators 284a-284h so as to allow selected degrader plate(s) to be inserted in (e.g., FIG. 10C) and out (e.g., FIG. 10B) of an active area 300 where the beam of protons 128 can pass. An extendable portion of a given actuator 284 is shown to be attached to a top portion of the corresponding plate 282 via a mounting plate 292 and a bracket 302, and a fixed base portion of the actuator 282 is shown to be attached to a mounting bar 290. The mounting bar 290 is shown to be attached to a structural frame 286, which is in turn mounted to a mounting assembly (FIGS. 10B and 10C) via mounting bolts 288. Thus, when mounted in the foregoing manner, the active area 300 can accommodate passage of protons which in some situations can be spread to provide hit events for most or all of the crystals 238 of the calorimeter 228.

When the calibration device 280 is mounted so as to provide the foregoing functionality, it is preferable to have the degrader plates 282 be positioned in the active area 300 precisely in some selected orientation. For example, a degrader plate 282 can be oriented so that its plane defined is substantially perpendicular to a beam axis at the center of the active area 300. To facilitate such positioning, lateral movements of the degrader plates 282 can be guided at their bottom portions by guide slots 296 (FIG. 10A) dimensioned to receive and guide their corresponding guide members attached to the bottom edges of the plates 282 by mounting plates 294.

In the example calibration device 280, the actuators 284 are based on commercially available Firgelli L-16 linear motion actuators set for a linear stroke of about 10 cm. It will be understood that mechanical mounting and electrical operation of such actuators can be implemented in a number of known ways by one of ordinary skill in the art. It will also be understood that other actuation devices and methodologies (e.g., mechanical, electrical, magnetic, hydraulic, pneumatic, or any combination thereof) can also be utilized.

Figure 11:
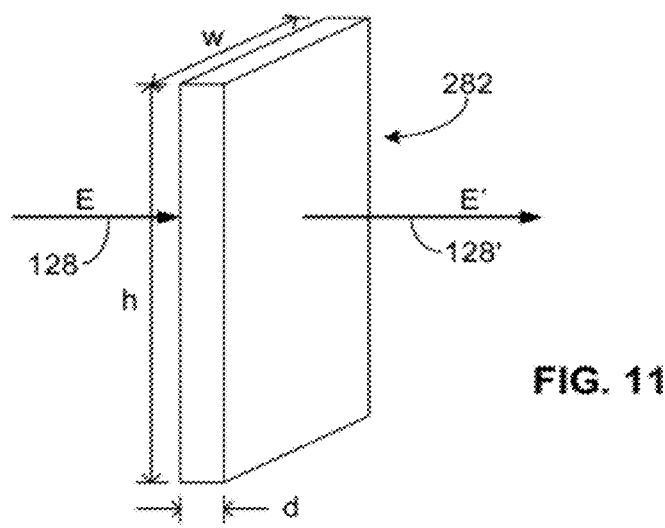
FIG. 11 shows a degrader plate that can be used in the calibration systems of FIGS. 8 and 9.

FIG. 11 shows a single degrader plate 282. The example plate 282 is shown to have a lateral dimension of height h and width w. The plate 282 is also shown to have a thickness d. For the example plates 282a-282h, the height (h) is approximately 20 cm, and the width (w) is approximately 10 cm for each plate. Approximate thickness (d) values of eight example plates 282a-282h are listed in Table 1, where the value of one thickness unit ($d_0$) is approximately 0.3175 cm. The thicknesses (d1-d8) of the example plates 282a-282h were measured to an accuracy of better than approximately ±0.05 mm by obtaining a mean of ten random measurements across a given plate with a digital height gauge.

TABLE 1

| Plate | Thickness | Value |
|---|---|---|
| 282a | d1 | $16 \times d_0$ |
| 282b | d2 | $d_0$ |
| 282c | d3 | $16 \times d_0$ |
| 282d | d4 | $2 \times d_0$ |
| 282e | d5 | $16 \times d_0$ |
| 282f | d6 | $4 \times d_0$ |
| 282g | d7 | $16 \times d_0$ |
| 282h | d8 | $8 \times d_0$ |

As one can see, different effective thicknesses in a range from zero to $79d_0$ can be provided by providing various combinations of the example plates 282a-282h. For example, first few thicknesses in increments of $d_0$ can be achieved by d2, d4, d2+d4, d6, d2+d6, d4+d6, d2+d4+d6, d8, etc. In terms of WET values, such plates can provide different effective water-equivalent thicknesses between about 0 cm and 26 cm (for 200 MeV protons), or about 0 cm and 8 cm (for 100 MeV protons), by combining different degrader plates. In some implementations the degrader plates can be dimensioned so as to allow different plate combinations whose WET values range from about zero to an upper limit that yields X % of a maximum detector response value without any degrader. In some implementations, the value of X can be, for example, 20, 10, or 5.

The example degrader plates as described herein are machined from polystyrene material having substantially uniform density. It will be understood that other degrader materials having greater or lesser WET values can also be utilized.

As shown in FIG. 11, a proton with energy E (arrow 128) ends with energy E' (arrow 128') upon passage through the degrader plate 282, where E' is less than E. Generally, the difference between E and E' is attributable to energy degradation in the degrader plate 282. Thus, a larger overall thickness of the degrader plate(s) results in a larger energy degradation or loss.

Figure 12A:
FIGS. 12A-12C show examples of how different amount of energy degradation can be introduced to a beam of protons by inserting selected degrader plates into the beam.
Figure 12B:
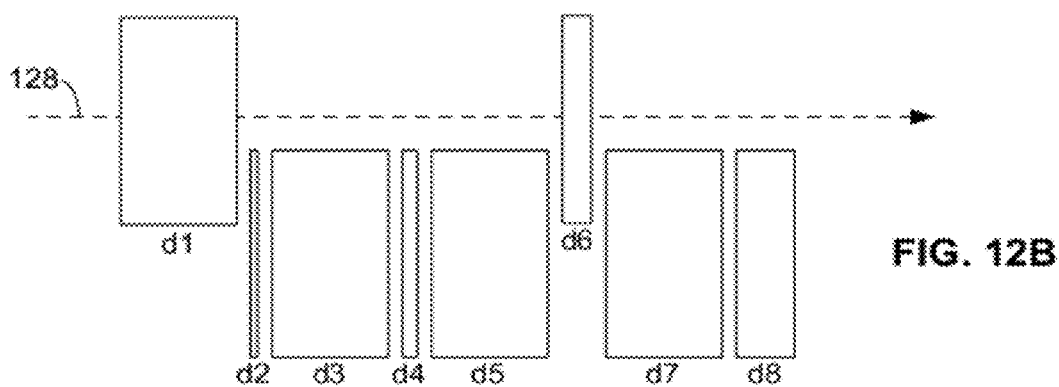
Figure 12C:
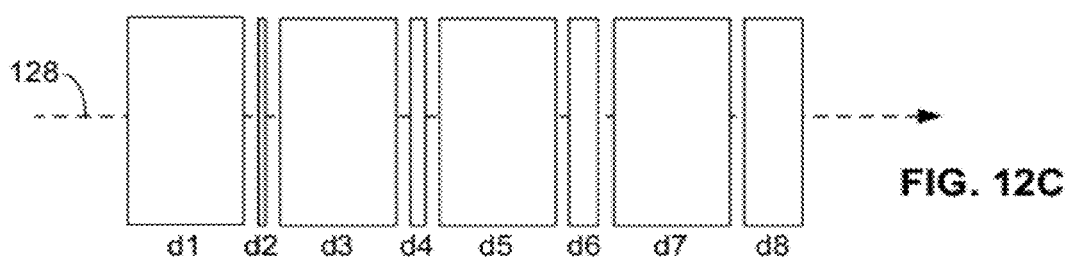

FIGS. 12A-12C show examples of how different effective degrader thicknesses can be achieved by utilizing the example calibration device 280 described in reference to FIGS. 9-11. In FIG. 12A, all of the plates 282a-282h are shown to be moved out of the beam path 128, thereby yielding an effective degrader thickness of approximately zero. In FIG. 12C, all of the plates 282a-282h are shown to be moved in the beam path 128, thereby yielding an effective degrader thickness of approximately $79d_0$. The foregoing example combinations of plates allow introduction of different ranges of WET values for calibrating different proton energies. For example, a WET range of approximately 0 cm to approximately 26 cm can be introduced for 200 MeV protons, and a WET range of approximately 0 cm to approximately 8 cm can be introduced for 100 MeV protons.

FIG. 12B shows an example where an intermediate effective thickness is achieved by moving some of the plates in the beam path 128 while others remain out of the beam path 128. In the particular example, degrader plates 282a and 282f are in the beam path 128, thereby yielding an effective thickness of $20d_0$.

To calibrate a calorimeter such as the example calorimeter 228, different energy degradation settings can be provided by different combinations of the degrader plates as described herein. Energy measurements at such degradation settings can be obtained for a given beam energy (e.g., 200 MeV or 100 MeV). Because the effective WET values are known from the degrader plates used, a relationship between WET and calorimeter response can be obtained. For the calibration examples described herein, a given proton's path length was calculated using a most likely path (MLP) technique, and if the calculated path length exceeded the known net physical degrader thickness by more than 0.5%, the proton was not used for calibration. Such an example of selecting protons can allow calibration to be performed using protons that traverse degrader plate(s) having a known thickness essentially perpendicularly. Accordingly, for a proton traversing a degrader plate approximately perpendicularly, the plate's WET can be approximately the same as the proton's WEPL through the plate. Although described in the context of selecting protons that pass through degrader plate(s) perpendicularly, other non-perpendicular protons can also be selected, based on, for example, comparison of the proton's MLP with a projected straight line (e.g., based on the front tracker) through the degrader plate(s).

In the context of segmented calorimeters (such as the example calorimeter 228), responses from different crystals (or channels) can be different even if the input protons are identical. Such differences in responses among the channels can be due to a number of factors, such as variations in material property, variations in light collection efficiency, and/or variations in photo detector performance (quantum efficiency, gain, etc.). Accordingly, it is desirable to normalize such differences in responses associated with the different channels.

FIG. 13 shows a process 400 that can be implemented to perform a calibration as described herein. In block 402, a relative weighting factor can be determined for each crystal (or channel) for a given energy of proton beam to facilitate normalized energy measurements by the crystals. In block 404, different degraders can be introduced in the proton beam, with each having a known water-equivalent thickness (WET), to obtain responses of the channels to the different WET values. In block 406, a relationship between water-equivalent path length (WEPL) of a proton and measured energy based on the WET values and the relative weighting factors can be obtained. In some implementations, such measured energy can be expressed in different units based on the responses of the crystals.

In some situations, the energy of proton beam being delivered during a given operating period may vary somewhat from a desired setting. External factors such as variations in temperature can also influence calorimeter responses. Further, some or all of the foregoing example factors that can influence channels differently can also impact calorimeter responses. Accordingly, a calibration process as described herein can be performed to accommodate different operating situations. Two non-limiting examples of such situations are described in reference to FIGS. 14 and 15.

FIG. 14 shows a process 410 that can be performed as a part of an initialization of a proton CT system. In block 412, an initialization of a proton CT system can be performed. In block 414, a WEPL calibration as described herein can be performed. In block 416, calibration data resulting from the WEPL calibration can be stored. In some implementations, such data can be stored in a non-transitory computer readable medium. In block 418, the proton CT system can be operated based on the calibration data.

FIG. 15 shows a process 420 that can be performed after a change in proton beam energy. In block 422, proton beam energy can be changed to a new value. In block 424, a WEPL calibration as described herein can be performed. In block 426, calibration data resulting from the WEPL calibration can be stored. In some implementations, such data can be stored in a non-transitory computer readable medium. In block 428, the proton CT system can be operated at the new beam energy based on the calibration data.

As described herein, a relationship between weighted sum of crystal responses and water-equivalent thickness (WET) (of the material the protons had traversed before being stopped in the calorimeter) can be obtained. As also described herein, the WET of degrader plates (their physical thickness multiplied by the RSP of the degrader material) can be the controlled variable in the calibration process, and the response of the calorimeter (which can be subject to statistical variation) can be the dependent variable. Accordingly, the uncertainty of an individual WEPL measurement can be derived by propagating the uncertainty of the calorimeter response into the relationship that yield the corresponding WEPL value.

Figure 16:
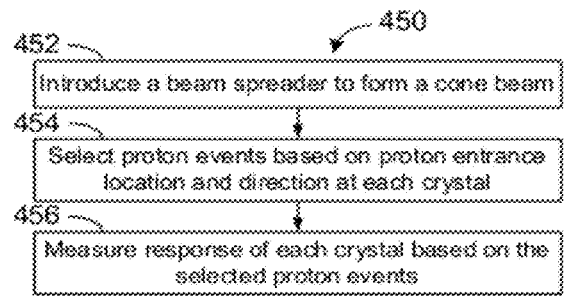
FIG. 16 shows a process that can be implemented to estimate a response weighting factor for each crystal of the energy detector.
Figure 17:
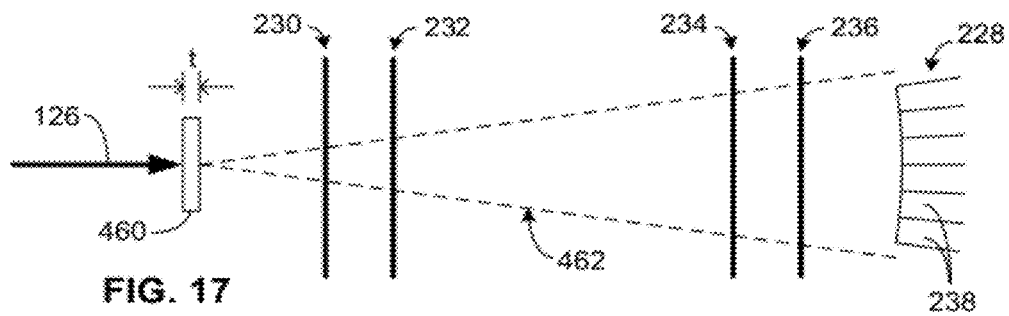
FIG. 17 shows an example of how the beam can be configured to facilitate the process of FIG. 16.
Figure 18:
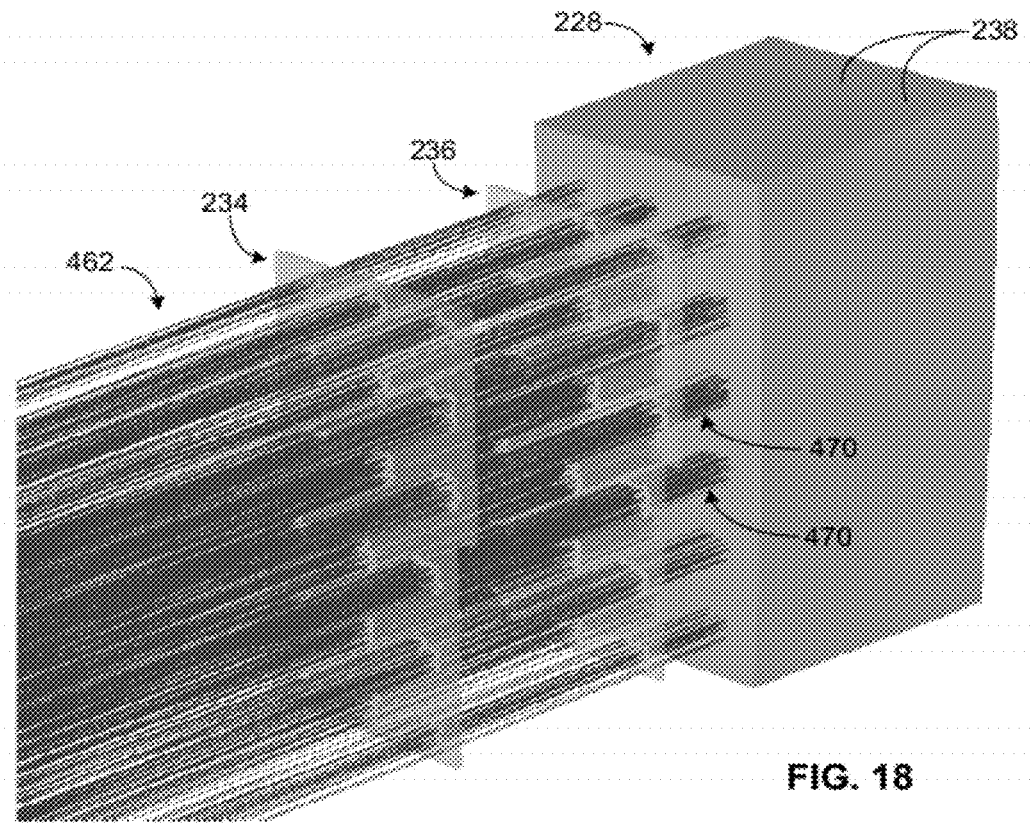
FIG. 18 shows a computer generated graphic of proton events selected to perform the process of FIG. 16.

In some implementations, a calibration process that generates the foregoing relationship between the calorimeter response and the WEPL can include two stages. The first stage can include normalization of the channels of the calorimeter 228. Such a normalization process can include determination of a relative weighting factor for each channel (crystal) of the calorimeter. FIGS. 16-18 show an example of how such weighting factors can be determined. The second stage can include introducing different WET-valued degrader plates for the proton beam and obtaining normalized responses from the calorimeter. FIGS. 19-22 show an example of how such normalized responses can be determined.

FIG. 16 shows a process 450 that can be implemented to normalize the responses of the different channels of the calorimeter. In block 452, a beam spreader can be introduced in the beam of protons to form a cone shaped beam. Such a configuration is shown in FIG. 17, where an input beam 126 is spread by a beam spreader 460 at a location upstream of the front tracker (230, 232). The beam spreader 460 can be a lead foil having a thickness t, and the value of t can be approximately 1.9 mm for 200 MeV protons, and approximately 0.2 mm for 100 MeV protons. A cone beam resulting from such a beam spreader 460 is depicted by a cone 462. Such a cone can be selected to provide sufficient proton events at the upper and lower crystals 238 of the calorimeter 228. For this stage of calibration, no degrader plate is placed in the beam.

In block 454 of the process 450, proton events can be selected based on proton entrance location and direction at each crystal. For example, protons whose tracks (obtained from the front and rear trackers) that enter a crystal near its center and have entrance angles approximately parallel to the crystal's axis can be selected. In FIG. 18, such proton events are depicted as tracks 470 entering center regions of their respective crystals 238. Also, the tracks 470 are generally parallel to the axes of the crystals 238.

In block 456 of the process 450, response of each crystal can be obtained based on the selected proton events. For an i-th crystal (i=1, . . . , N), where N is the total number of crystals in the calorimeter, a relative weighting factor for the raw response can be defined as $$w_i = \frac{10E}{\langle r \rangle_i} \tag{4}$$

where E is the beam energy at which the calibration is being performed, and $\langle r \rangle_i$ is the average signal of the i-th crystal. The factor 10E can be arbitrary so that, for example, the mean weighted sum of all crystal responses to a proton of 200 MeV is approximately 2,000. Other factors can also be utilized.

Figure 19:
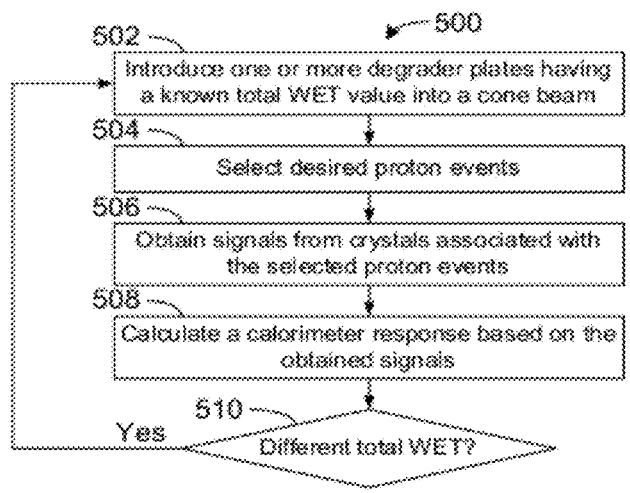
FIG. 19 shows a process that can be implemented to calculate a response of the energy detector when the proton beam is subjected to different degrader values.
Figure 20:
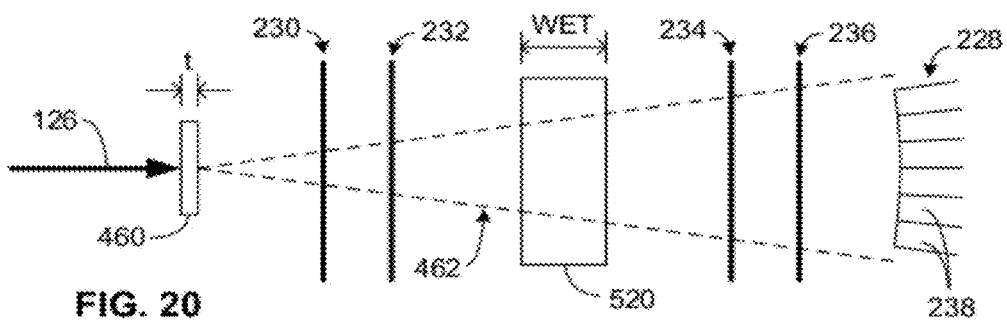
FIG. 20 shows an example of how the beam and the degrader can be configured to facilitate the process of FIG. 19.

FIG. 19 shows a process 500 that can be implemented to obtain a normalized calorimeter response for a given degrader WET value at a given beam energy. In block 502, one or more degrader plates having a known total WET value can be introduced into a cone beam of protons. FIG. 20 shows a cone beam configuration similar to that described in reference to FIG. 17, but with a degrader 520 (having a total WET value) positioned between the front and rear trackers.

In block 504, desired proton events can be selected. For example, tracking and calorimeter response data can be collected for about $10^5$ proton for each degrader WET value. A series of data cuts can be made to the response data of the calorimeter to individual proton events to, for example, exclude events where the proton was scattered out of the scanner system, where pile-up occurred in the tracker (and therefore yielding ambiguous tracking information), where the proton did not pass through all eight layers of silicon tracking detector, or where the calculated most likely path (MLP) length exceeded the known degrader thickness by greater than approximately 0.5%. The example path length based cut allows selection of protons that passed essentially straight and perpendicularly through the degrader plate(s).

In block 506, signals from crystals associated with the selected proton events can be obtained. In block 508, a normalized calorimeter response can be calculated based on the obtained signals. For the proton events that remain after the foregoing example cuts, a calorimeter response r can be calculated by forming a weighted sum of crystals' signals higher than 3σ above the noise floor using the weighting factors defined by Equation 4 and obtained as described in reference to FIGS. 16-18.

Figure 21:
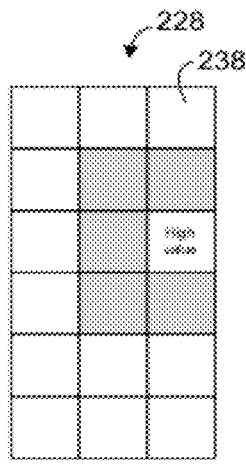
FIG. 21 shows an example of how signals from the energy detector can be selected to perform the process of FIG. 19.

For a given proton event, a crystal having the largest response is identified. In an example shown in FIG. 21, suppose that the crystal 238 denoted as "high value" has the largest response. Signal from such a crystal, and signals only from crystals that are contiguous with the "high value" crystal, are included in the foregoing weighted sum. In the example of FIG. 21, the shaded crystals surrounding the "high value" crystal are the crystals whose signals are included in the weighted sum if the signals are above the noise threshold.

Figure 22:
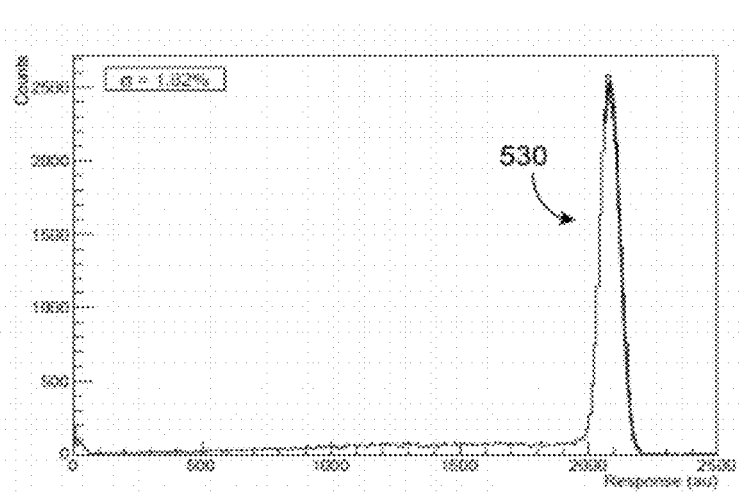
FIG. 22 shows an example of the energy detector response.

FIG. 22 shows an example histogram 530 of the summed calorimeter response (in arbitrary units) to a given degrader WET. Based on such a distribution, a mean calorimeter response for each degrader thickness can be obtained by fitting a Gaussian distribution to the peak of the distribution. To exclude the non-Gaussian low-energy back tail (which becomes more pronounced after protons went through a degrader of greater thickness) only the part of the spectrum that is symmetric with respect to the peak is included in this Gaussian fit, effectively removing the lower energy tail.

In some implementations, steps 502 to 508 of FIG. 19 can be repeated for different WET values. In some implementations, repeating of such steps can be performed automatically by utilizing an automatic controllable calibration device such as the example described in reference to FIGS. 9-12. For such repeating implementations, the process 500 can determine in a decision block 510 whether another calorimeter response should be obtained using a different total WET value. If the answer is "Yes," steps 502 to 508 can be repeated.

Figure 23:
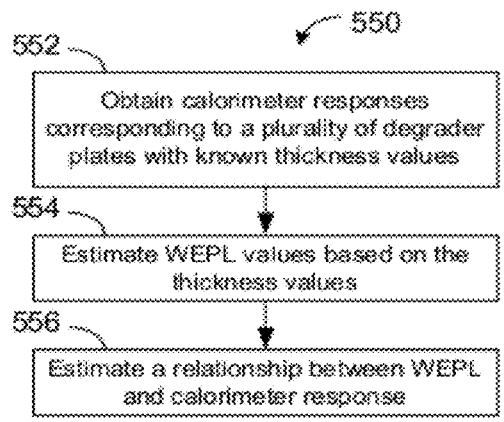
FIG. 23 shows a process that can be implemented to estimate a relationship between the energy detector response and WEPL.

Normalized calorimeter responses obtained in the foregoing manner can be used to generate a relationship between WEPL and response of a calorimeter. FIG. 23 shows a process 550 that can be implemented to obtain such a relationship. In block 552, calorimeter responses corresponding to a plurality of degrader plates with known thickness values can be obtained. In block 554, WEPL values can be estimated based on the known thickness values. As described herein, protons that pass through degrader plate(s) essentially straight and perpendicularly can be selected for calibration. For such a configuration, the net thickness of the degrader plate(s) or the calculated MLP can be converted to WEPL since the WET of each plate is known. In block 556, a relationship between WEPL and calorimeter response can be estimated.

Figure 24:
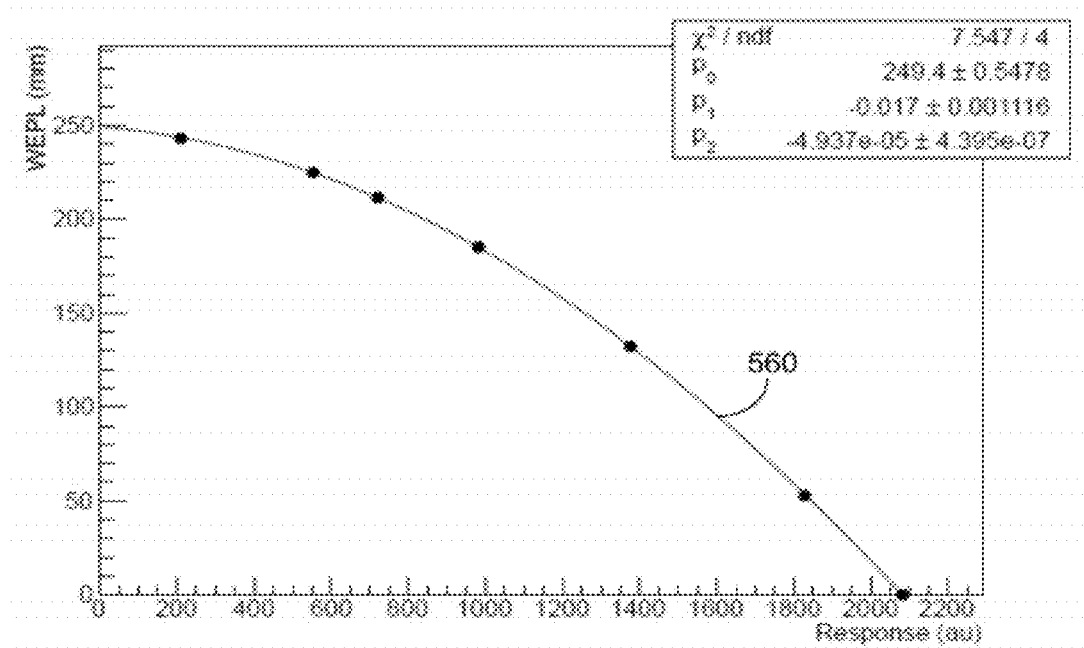
FIG. 24 shows an example of the relationship of FIG. 23 for 200 MeV protons.

FIG. 24 shows a plot of a plurality of data points corresponding to different WEPL values and their corresponding calorimeter response values. As expected, a higher WEPL results in a lower response, since the residual energy after passage through a corresponding degrader is lower.

The example data points of FIG. 24 can be fit in a number of different ways. In some implementations, the response/WEPL data points can be fit by a 2nd-degree polynomial guided by the form of the Bethe-Bloch equation to describe a relationship between the mean calorimeter response r and WEPL L (represented by the WET of the degrader). Such a fit curve is indicated by a curve 560 in FIG. 24, and can be represented as $$L(r) = p_2 r^2 + p_1 r + p_0 \quad (5)$$

where p0, p1 and p2 are fit parameters. When fit using a least-squares fitting method, the fit parameters p0, p1 and p2 are as shown in FIG. 24 for 200 MeV protons detected by the example calorimeter 228.

Once such a fitted calibration is obtained, the calorimeter's response to subsequent proton events can be quickly converted to a corresponding WEPL. Statistical uncertainty of this value can also be derived. For the example calibration relationship described herein, a mean variance of the calorimeter response ($\sigma^2_r$) can propagate to a variance of the WEPL, and the resulting uncertainty of the individual WEPL measurement can be expressed as $$\sigma^2_L = \sigma^2_r (2 p_2 r + p_1)^2. \quad (6)$$

Figure 25:
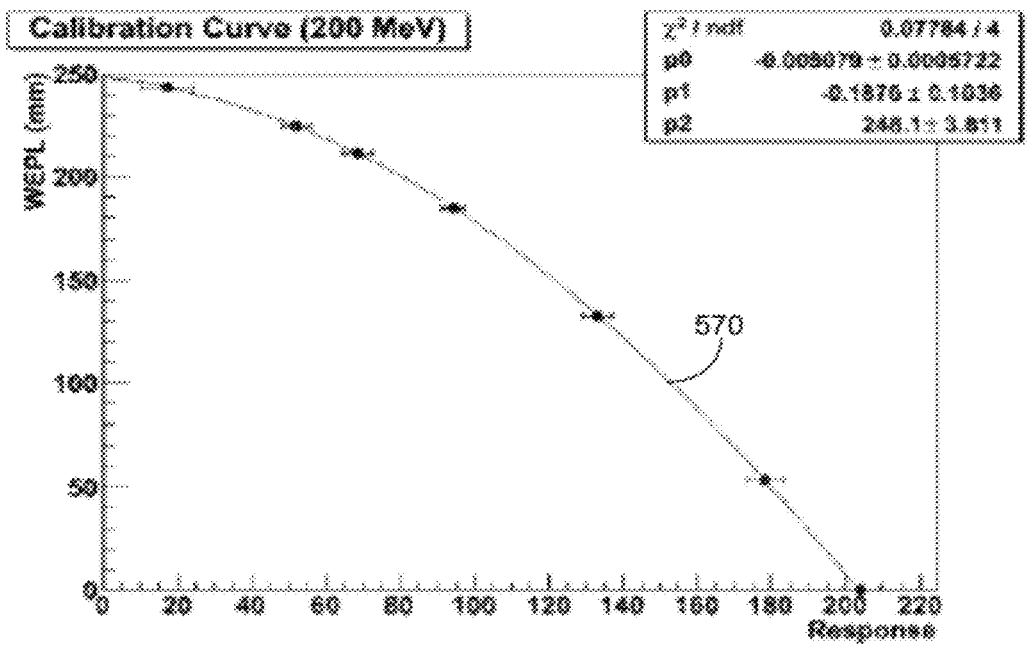
FIG. 25 shows another example of the relationship of FIG. 23 for 200 MeV protons.

The example calibration curve 560 is in the context of the calorimeter response being expressed in some arbitrary unit. For example, the weighting factor for each crystal is multiplied by a factor of 10 E so that the mean weighted sum of all crystal responses to a 200 MeV proton is approximately 2,000. It will be understood that other units and/or scales can also be utilized. For example, FIG. 25 shows a calibration curve 570 for the same calorimeter responding to 200 MeV protons. One can see that by removing the factor of 10 from the weighting factor calculation, the calorimeter scale can be reduced by a factor of 10.

Figure 26:
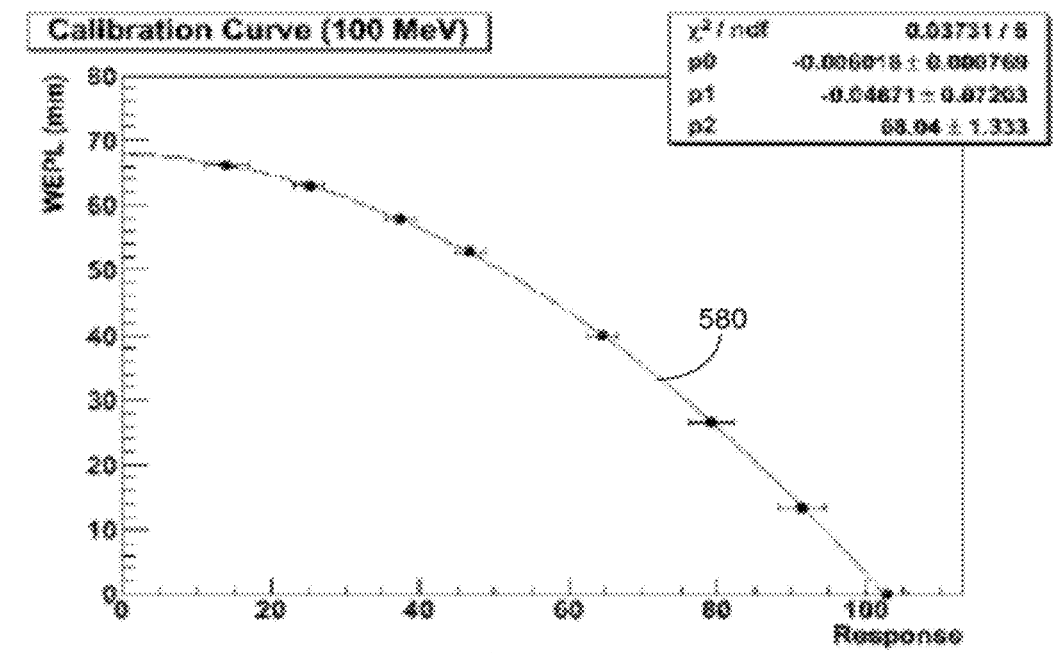
FIG. 26 shows an example of the relationship of FIG. 23 for 100 MeV protons.

FIG. 26 shows a similar calibration curve 580 for the same calorimeter responding to 100 MeV protons. Similar calibration curves can be obtained for protons having other energies. For example, proton energy can be chosen according to a WET of an object to be imaged with the pCT scanner; and calibration as described herein can be performed accordingly.

To verify the foregoing example calibration method, the WET of a set of tissue-equivalent plates (Gammex Inc., Middleton, Wis., USA) was derived from the pCT scanner calibration curve obtained with 100 MeV protons and compared to results using a water phantom depth-dose range shift measurement. The tissue-equivalent degraders included 1 cm thick plates of muscle, adipose, brain, and compact bone material, and a 2 cm thick plate of lung. Each plate was inserted into the scanner, one at a time, and approximately 30,000 proton histories were recorded with 100 MeV protons. The weighted calorimeter response for each plate was converted to WEPL using the 100-MeV calibration curve. The mean WEPL for each plate was found by fitting a Gaussian distribution to the converted WEPL values. The RSP, ρ, was calculated using the formula $$\rho = L/t_p, \quad (7)$$

where $t_p$ is the physical thickness of the plate. The water-tank measurements were performed with a beam energy of 186 MeV and a 60 mm modulation wheel to produce a spread out Bragg peak (SOBP). The range shift as a result of inserting the tissue plate into the beam path was then measured by scanning a Markus chamber along the beam axis inside a water phantom. The plates were placed outside the water tank. The RSP, ρ, was determined using the formula $$\varrho = \frac{R_{50,w} - R_{50,p}}{t_p}, \quad (8)$$

where $R_{50,w}$ is depth to 50% ionization in water, and $R_{50,p}$ is the depth to 50% ionization in water behind the plate.

Figure 27:
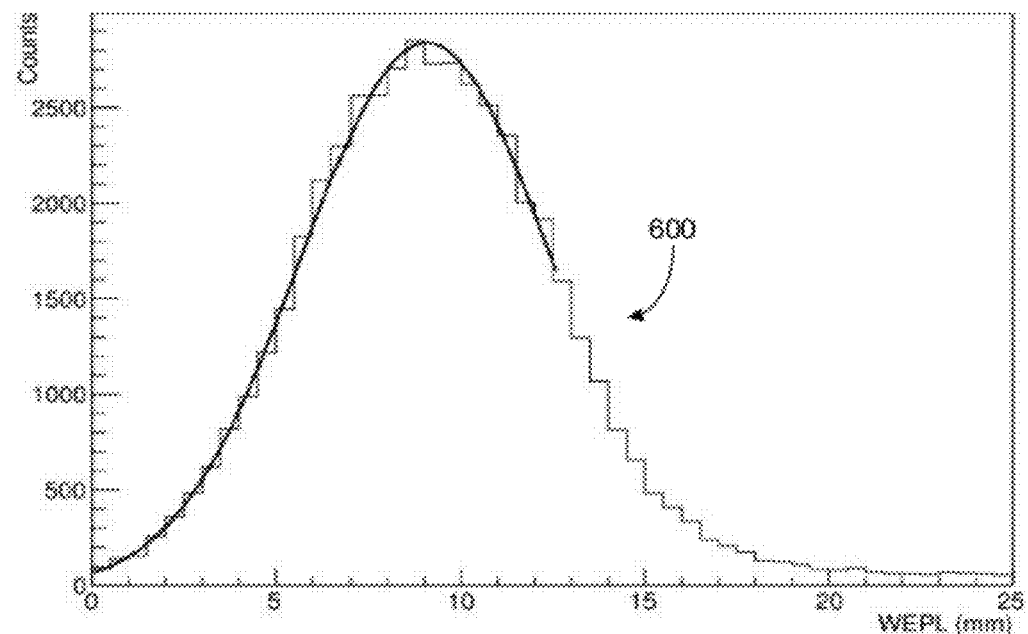
FIG. 27 shows a WEPL distribution obtained as described herein for an example muscle equivalent plate.
Figure 28:
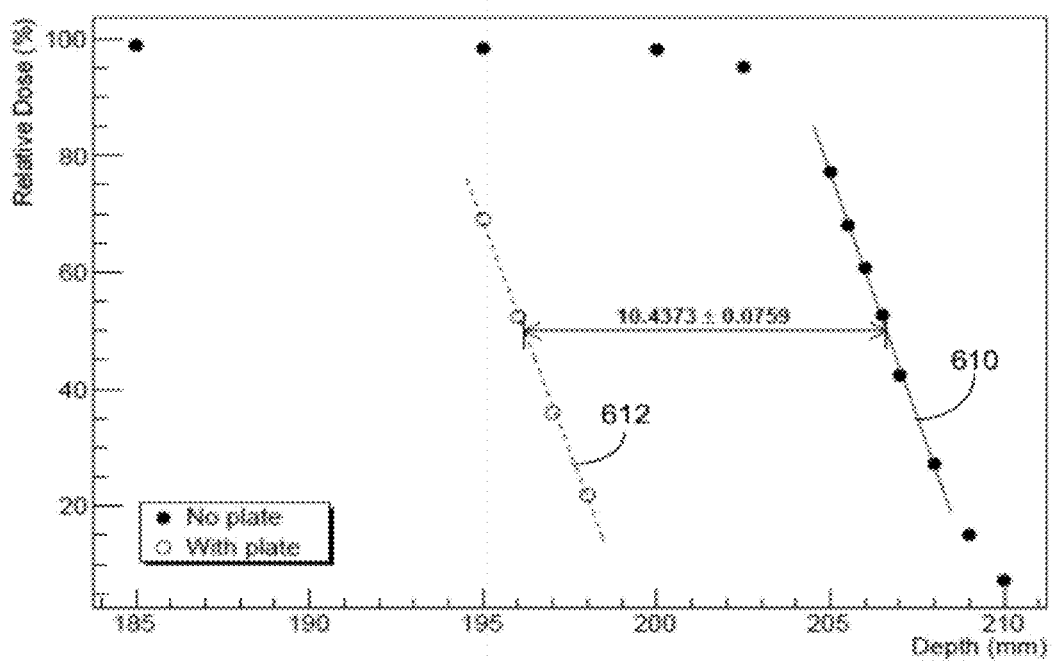
FIG. 28 shows a shift of the distal edge of the Bragg peak from the plate of FIG. 27 from a no-plate line.

FIG. 27 shows a WEPL distribution 600 for the example muscle equivalent plate, being representative of the distributions obtained with the other example plates. FIG. 28 shows a shift of the distal edge of the Bragg peak from the same plate (line 612) from the no-plate line 610.

Table 2 compares the WET values obtained with the pCT measurement as described herein and the foregoing water-tank measurement. Both methods agree to better than about ±0.5. Note that the RSP uncertainty is smaller for the results obtained with the pCT scanner, while the dose to the phantom was significantly lower, by a factor of approximately $10^5$.

TABLE 2

| Material | RSP via range shift method | $\sigma_{RSP}$ via range shift method | RSP via pCT method | $\sigma_{RSP}$ via pCT method |
| --- | --- | --- | --- | --- |
| Lung | 0.267 | 0.005 | 0.268 | 0.001 |
| Adipose | 0.947 | 0.007 | 0.943 | 0.002 |
| Muscle | 1.032 | 0.008 | 1.037 | 0.002 |
| Brain | 1.062 | 0.007 | 1.064 | 0.002 |
| Liver | 1.076 | 0.005 | 1.078 | 0.002 |
| Cortical bone | 1.599 | 0.007 | 1.595 | 0.002 |

A second test of the validity of the calibration procedure as described herein was performed by acquiring a pCT scan of an acrylic cylinder with 0.5 cm thick walls and 15 cm diameter filled with distilled water and degassed in a vacuum chamber. The water phantom was scanned with a cone beam of 200 MeV protons in 90 angular steps over 360 degrees. A total number of about 40 million proton histories were utilized for the image reconstruction of RSP values across the phantom using an iterative DROP (diagonally relaxed orthogonal relaxation) algorithm combined with a superiorization of total variation as described in U.S. Patent Publication No. 2011-0220794. The phantom was reconstructed in 3D with a 16×16×8 cm$^3$ reconstruction volume. The volume was divided into voxels of 0.625×0.625×2.5 mm$^3$ size.

Figure 29:
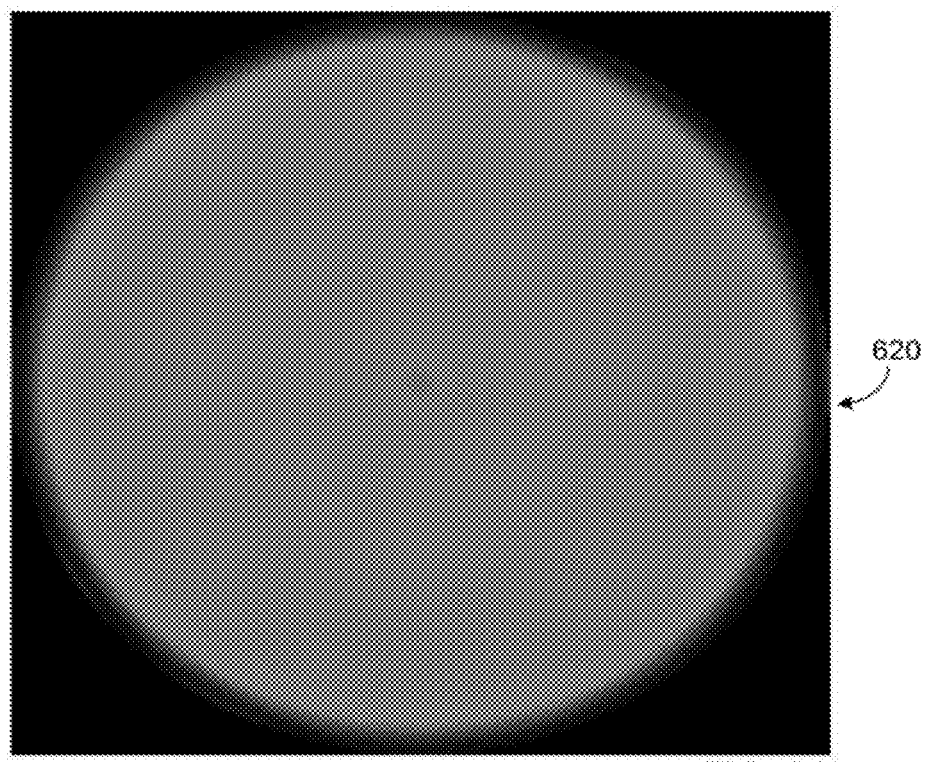
FIG. 29 shows an axial slice from a reconstructed water phantom utilizing calibration features as described herein.

FIG. 29 shows an axial slice 620 from the reconstruction of the water phantom. A close inspection shows that there are systematic ring artifacts in the reconstruction. The central artifact is believed to be related to the overlap region of the tracker planes mentioned herein. The outer ring artifacts are most likely due to incomplete compensation of the variations in the signal from individual calorimeter crystals.

Figure 30:
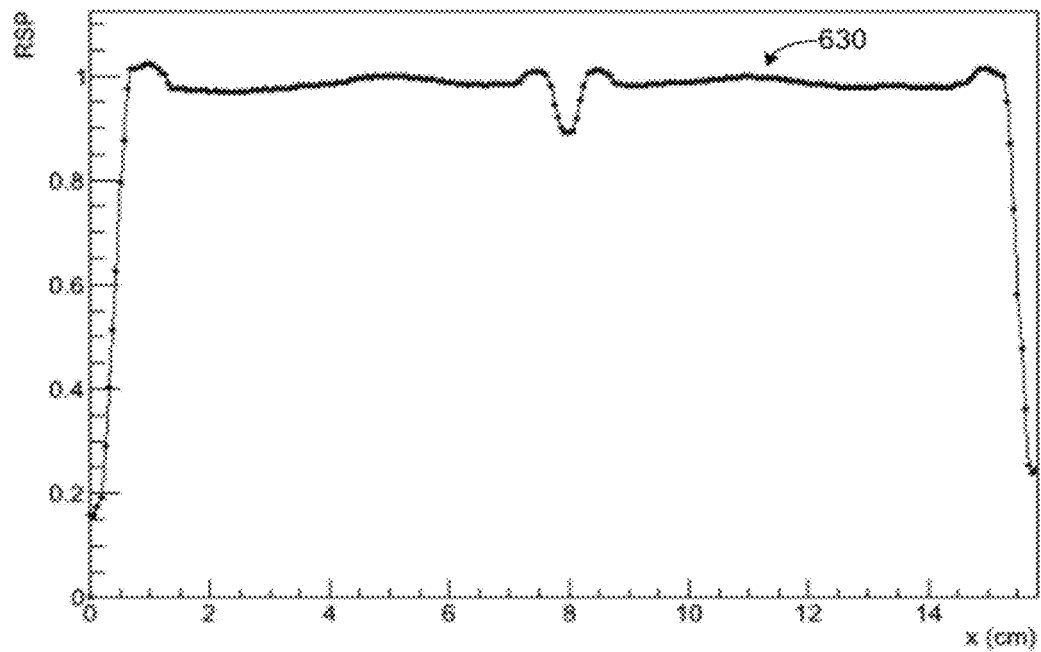
FIG. 30 shows a central band profile of the axial slice of FIG. 29.

FIG. 30 shows a central band profile 630 across an axial slice. Again the central artifact as well as the ring artifacts are seen. Excluding the central artifact, reconstructed RSP values for the water phantom agreed with the expected value of 1 to within about ±1%.

Figure 31:
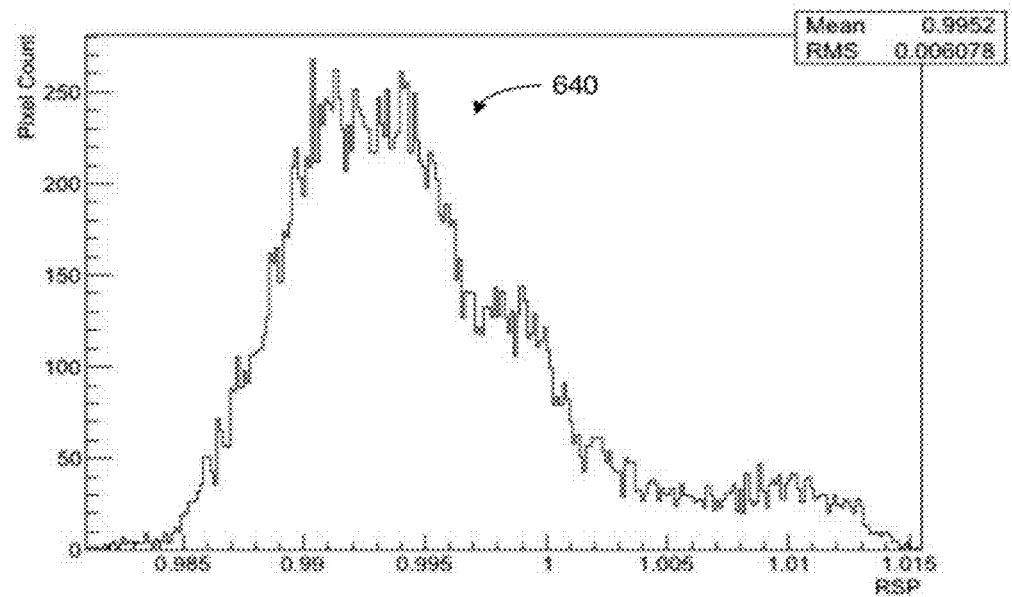
FIG. 31 shows a histogram of RSP values selected from a region of interest excluding the central artifact and acrylic walls of the example water phantom of FIGS. 29 and 30.

FIG. 31 shows a histogram 640 of RSP values selected from a region of interest excluding the central artifact and acrylic walls described in reference to FIGS. 29 and 30. As seen in the histogram legend, the mean RSP value is approximately 0.995 with an RMS variation of approximately 0.006.

Figure 32:
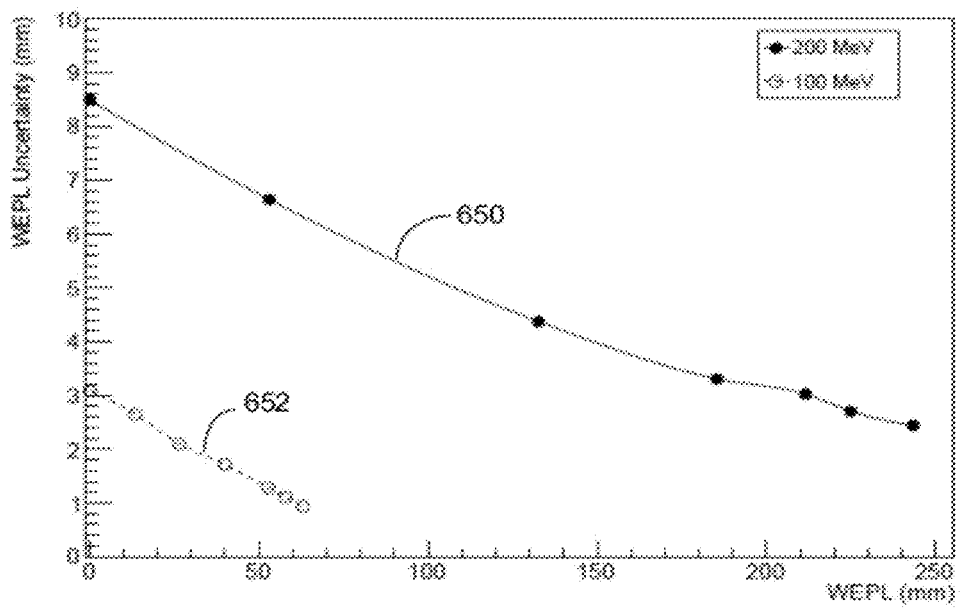
FIG. 32 shows example WEPL uncertainty curves value for beam energies of 100 MeV and 200 MeV.

FIG. 32 shows curves 650, 652 demonstrating example dependence of single-proton WEPL uncertainty ($\sigma_L$) on the WEPL value for beam energies of 100 MeV and 200 MeV. Note that the uncertainty of a WEPL measurement with N protons scales approximately with 1/sqrt(N).

It is also noted that, as expected from Equation 6, the WEPL uncertainty decreases for larger path lengths (hence, smaller response). The contribution of the spread of the initial proton energy to this uncertainty should be negligible at 200 MeV, since the momentum spread of the Loma Linda University proton synchrotron is known to be about 0.01% (which translates to an energy spread of about 0.040 MeV (1 sigma)). At zero or small WEPL (no or thin degrader), the uncertainty may be due to a combination of intrinsic noise of the calorimeter and energy straggling in the materials between the accelerator and the calorimeter, including secondary emission monitor at beam exit, the vacuum exit window, lead scattering foil, air, and the silicon tracker modules. The combined energy straggling in these materials at 200 MeV energy is estimated to be about 0.52 MeV (0.26%). As the relative uncertainty of calorimeter response at small WEPL is about 2%, the largest contribution to the uncertainty at small WEPL may be the intrinsic resolution of the calorimeter, which can be mostly defined by the process of light collection. Some additional uncertainty can arise from, for example, leakage of energy due to large-angle elastic scattering of primary protons and inelastic nuclear interactions in the calorimeter leading to the production of neutrons and gamma rays, which leave the calorimeter. These events are expected to contribute to the low-energy tail visible in the calorimeter spectrum, but can also broaden the main peak to some degree. For larger WEPL values, the uncertainty of the calorimeter response can increase due to increasing energy straggling in the degrader, but this can be compensated by the increasing sensitivity of the energy deposited in the calorimeter to changes in WEPL, thus leading to an overall decrease in WEPL uncertainty. One should also note that by recording a larger number of proton events, very precise RSP determinations of any material can be performed.

In current practice, water-equivalent density is typically derived by conversion of the Hounsfield values of an X-ray CT scan, which can lead to average systematic range uncertainties of the order of 3%-4% in relatively uniform tissues, and possibly higher uncertainties in the presence of larger heterogeneities. It is believed that proton CT can reduce the uncertainty related to conversion of Hounsfield values by measuring the residual energy (or a quantity that is related to it) and converting it to WEPL of protons traversing a heterogeneous sample using an adequate calibration of the detector response against WET of known materials. The pCT scanner can then be used to reconstruct RSP by acquiring many proton histories from multiple directions. It can also be used to accurately measure the WET of materials of not exactly known composition that may be present in the beam path during treatment.

The calibration methodologies described herein can provide a number of advantageous features over other calibration methods. For example, the pCT scanner measurement as described herein is much faster than the water tank based method. It can only takes a few seconds to collect the proton histories required for an accurate RSP measurement, while the water tank measurements can require about 15 minutes per WET determination for 10-15 individual measurements along the distal fall-off of the original and shifted SOBP.

The present disclosure describes various features, no single one of which is solely responsible for the benefits described herein. It will be understood that various features described herein may be combined, modified, or omitted, as would be apparent to one of ordinary skill. Other combinations and sub-combinations than those specifically described herein will be apparent to one of ordinary skill, and are intended to form a part of this disclosure. Various methods are described herein in connection with various flowchart steps and/or phases. It will be understood that in many cases, certain steps and/or phases may be combined together such that multiple steps and/or phases shown in the flowcharts can be performed as a single step and/or phase. Also, certain steps and/or phases can be broken into additional sub-components to be performed separately. In some instances, the order of the steps and/or phases can be rearranged and certain steps and/or phases may be omitted entirely. Also, the methods described herein are to be understood to be open-ended, such that additional steps and/or phases to those shown and described herein can also be performed.

Some aspects of the systems and methods described herein can advantageously be implemented using, for example, computer software, hardware, firmware, or any combination of computer software, hardware, and firmware. Computer software can comprise computer executable code stored in a computer readable medium (e.g., non-transitory computer readable medium) that, when executed, performs the functions described herein. In some embodiments, computer-executable code is executed by one or more general purpose computer processors. A skilled artisan will appreciate, in light of this disclosure, that any feature or function that can be implemented using software to be executed on a general purpose computer can also be implemented using a different combination of hardware, software, or firmware. For example, such a module can be implemented completely in hardware using a combination of integrated circuits. Alternatively or additionally, such a feature or function can be implemented completely or partially using specialized computers designed to perform the particular functions described herein rather than by general purpose computers.

Multiple distributed computing devices can be substituted for any one computing device described herein. In such distributed embodiments, the functions of the one computing device are distributed (e.g., over a network) such that some functions are performed on each of the distributed computing devices.

Some embodiments may be described with reference to equations, algorithms, and/or flowchart illustrations. These methods may be implemented using computer program instructions executable on one or more computers. These methods may also be implemented as computer program products either separately, or as a component of an apparatus or system. In this regard, each equation, algorithm, block, or step of a flowchart, and combinations thereof, may be implemented by hardware, firmware, and/or software including one or more computer program instructions embodied in computer-readable program code logic. As will be appreciated, any such computer program instructions may be loaded onto one or more computers, including without limitation a general purpose computer or special purpose computer, or other programmable processing apparatus to produce a machine, such that the computer program instructions which execute on the computer(s) or other programmable processing device(s) implement the functions specified in the equations, algorithms, and/or flowcharts. It will also be understood that each equation, algorithm, and/or block in flowchart illustrations, and combinations thereof, may be implemented by special purpose hardware-based computer systems which perform the specified functions or steps, or combinations of special purpose hardware and computer-readable program code logic means.

Furthermore, computer program instructions, such as embodied in computer-readable program code logic, may also be stored in a computer readable memory (e.g., a non-transitory computer readable medium) that can direct one or more computers or other programmable processing devices to function in a particular manner, such that the instructions stored in the computer-readable memory implement the function(s) specified in the block(s) of the flowchart(s). The computer program instructions may also be loaded onto one or more computers or other programmable computing devices to cause a series of operational steps to be performed on the one or more computers or other programmable computing devices to produce a computer-implemented process such that the instructions which execute on the computer or other programmable processing apparatus provide steps for implementing the functions specified in the equation (s), algorithm(s), and/or block(s) of the flowchart(s).

Some or all of the methods and tasks described herein may be performed and fully automated by a computer system. The computer system may, in some cases, include multiple distinct computers or computing devices (e.g., physical servers, workstations, storage arrays, etc.) that communicate and interoperate over a network to perform the described functions. Each such computing device typically includes a processor (or multiple processors) that executes program instructions or modules stored in a memory or other non-transitory computer-readable storage medium or device. The various functions disclosed herein may be embodied in such program instructions, although some or all of the disclosed functions may alternatively be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." The word "coupled", as generally used herein, refers to two or more elements that may be either directly connected, or connected by way of one or more intermediate elements. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or" in reference to a list of two or more items, that word covers all of the following interpretations of the word: any of the items in the list, all of the items in the list, and any combination of the items in the list. The word "exemplary" is used exclusively herein to mean "serving as an example, instance, or illustration." Any implementation described herein as "exemplary" is not necessarily to be construed as preferred or advantageous over other implementations.

The disclosure is not intended to be limited to the implementations shown herein. Various modifications to the implementations described in this disclosure may be readily apparent to those skilled in the art, and the generic principles defined herein may be applied to other implementations without departing from the spirit or scope of this disclosure. The teachings of the invention provided herein can be applied to other methods and systems, and are not limited to the methods and systems described above, and elements and acts of the various embodiments described above can be combined to provide further embodiments. Accordingly, the novel methods and systems described herein may be embodied in a variety of other forms; furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure.

What is claimed is:

1. A method for calibrating a proton computed tomography scanner, the method comprising:
   performing, for each of a plurality of energy degradation settings:
      introducing one or more degrader plates into a beam of protons having energy E, the one or more degrader plates in combination having a known water-equivalent thickness (WET) value; and
      obtaining signals from an energy detector for each of a plurality of selected protons that have passed through the one or more degrader plates and captured by the energy detector;
   calculating a weighted response of the energy detector based on at least some of the signals and one or more weighting factors associated with the energy detector; and
   generating a relationship between the weighted response and water-equivalent path length (WEPL) based on the known WET values associated with the plurality of energy degradation settings.

2. The method of claim 1, further comprising storing information representative of the relationship in a non-transitory computer-readable medium.

3. The method of claim 1, wherein introducing the one or more degrader plates includes positioning one or more substantially parallel polystyrene plates into the beam of protons such that the plates are approximately perpendicular to a longitudinal axis of the beam of protons.

4. The method of claim 3, wherein the WET values associated with the plurality of degradation settings are in a range between zero and an upper limit that yields a weighted response about 10% of a maximum weighted response obtained without any degrader plate.

5. The method of claim 1, wherein the energy detector includes a segmented calorimeter having a plurality of crystals such that the calorimeter includes a plurality of channels corresponding to the plurality of crystals.

6. The method of claim 5, wherein each of the crystals includes a cesium iodide (CsI) crystal.

7. The method of claim 5, wherein the plurality of selected protons includes protons that pass a proton event cut and having calculated most likely path lengths within Y% of a path length corresponding to the known WET value.

8. The method of claim 7, wherein the value of Y is approximately 0.5.

9. The method of claim 7, wherein the proton event cut includes one or more of excluding events where the proton was scattered out of the scanner, where proton tracking information is ambiguous, and where the proton did not pass through all tracking planes of the scanner.

10. The method of claim 5, wherein the beam of protons includes a cone beam dimensioned to allow hits of the selected protons at each of the crystals of the segmented calorimeter.

11. The method of claim 5, wherein the one or more weighting factors includes a weighting factor $w_i$ for the i-th channel of the calorimeter.

12. The method of claim 11, wherein the i-th weighting factor $w_i$ is represented as $w_i=(\text{scale factor})/<r>_i$, where the scale factor is selected to provide a desired scale of values for the weighted response of the energy detector, and $<r>_i$ represents an average signal of the i-th channel when the crystals are subjected to selected undegraded protons.

13. The method of claim 12, wherein the selected undegraded protons include protons that do not pass through any degrader and enter at center portions of and at directions generally parallel to their respective crystals.

14. The method of claim 13, wherein the scale factor is proportional to the beam energy E.

15. The method of claim 14, wherein the scale factor is selected to be C*E, where C is a constant selected so that a mean weighted sum of all of the channels yields a desired value.

16. The method of claim 11, wherein the weighted response of the energy detector includes a weighted sum of signals from selected channels.

17. The method of claim 16, wherein each of the signals has a value higher than $3\sigma$ above a noise floor value.

18. The method of claim 16, wherein the selected channels include a high value channel having the largest signal, and channels corresponding to crystals immediately surrounding the crystal of the high value channel.

19. The method of claim 5, wherein the relationship between the weighted response and WEPL includes a fit based on data points corresponding to the plurality of energy degradation settings.

20. The method of claim 19, wherein the fit includes a fit of a second-degree polynomial.

21. A proton computed tomography scanner comprising:
a tracker configured to facilitate tracking of individual protons of a beam before and after passage through a target region;
an energy detector configured to detect energy of the individual protons that have passed through the target region;
a calibration device configured to be positionable at or near the target region and allow introduction of a plurality of energy degradation settings for the beam or protons, the calibration device including a plurality of degrader plates configured to allow introduction one or more of the degrader plates into the beam, the one or more degrader plates in combination having a known water-equivalent thickness (WET) value;
a data acquisition system configured to obtain signals from the energy detector for each of a plurality of selected protons that have passed through the one or more degrader plates and captured by the energy detector; and
a processor configured to:
calculate a weighted response of the energy detector based on at least some of the signals and one or more weighting factors associated with the energy detector; and
generate a relationship between the weighted response and water-equivalent path length (WEPL) based on the known WET values associated with the plurality of energy degradation settings.

22. The scanner of claim 21, wherein the energy detector includes a segmented calorimeter having a plurality of crystals such that the calorimeter includes a plurality of channels corresponding to the plurality of crystals.

23. The scanner of claim 22, wherein each of the crystals includes a cesium iodide (CsI) crystal.

24. The scanner of claim 21, wherein the tracker includes a front tracker having a plurality of detections planes of silicon strips, and a rear tracker having a plurality of detection planes of silicon strips.

25. The scanner of claim 21, wherein the calibration device includes an actuator mechanically coupled to each of the plurality of degrader plates so as to allow remote controlling of the introduction of the one or more of the degrader plates into the beam.

26. The scanner of claim 21, wherein each the plurality of degrader plates is a polystyrene plate.

27. A calibration device for an ion based imaging system, the calibration device comprising:
a frame configured to allow the calibration device to be positioned at a target region of the imaging system and allow a beam of ions pass through the target region; and
a plurality of degrader plates configured to be movable into and out of the beam of ions, each degrader plate having a known water-equivalent thickness (WET) value such that combinations of the degrader plates allow introduction of a plurality of energy degradation settings for the beam of ions and estimation of a relationship between response associated with measurement of residual energy of individual ions and water-equivalent path length (WEPL).

28. The calibration device of claim 27, further comprising a plurality of actuators mechanically coupled to the plurality of degrader plates so as to allow remote controlling of the introduction of the energy degradation settings.

29. The calibration device of claim 27, wherein the ions include protons.

30. The calibration device of claim 27, wherein the imaging system includes a computed tomography imaging system.

* * * * *